United States Patent
Hacohen et al.

(10) Patent No.: US 9,132,009 B2
(45) Date of Patent: Sep. 15, 2015

(54) GUIDE WIRES WITH COMMISSURAL ANCHORS TO ADVANCE A PROSTHETIC VALVE

(75) Inventors: Gil Hacohen, Raanana (IL); Yossi Gross, Moshav Mazor (IL); Marco Papa, Milan (IT)

(73) Assignee: MITRALTECH LTD., Or Yehuda (IL)

( * ) Notice: Subject to any disclaimer, the term of this patent is extended or adjusted under 35 U.S.C. 154(b) by 0 days.

(21) Appl. No.: 12/840,463

(22) Filed: Jul. 21, 2010

(65) Prior Publication Data

US 2012/0022639 A1    Jan. 26, 2012

(51) Int. Cl.
*A61F 2/24* (2006.01)
*A61B 17/068* (2006.01)
*A61B 17/00* (2006.01)
*A61B 17/064* (2006.01)

(52) U.S. Cl.
CPC ............. *A61F 2/2466* (2013.01); *A61B 17/068* (2013.01); *A61F 2/2418* (2013.01); *A61F 2/2436* (2013.01); *A61B 2017/00243* (2013.01); *A61B 2017/0647* (2013.01); *A61B 2017/0649* (2013.01); *A61F 2/2409* (2013.01); *A61F 2/2427* (2013.01); *A61F 2/2457* (2013.01); *A61F 2/2487* (2013.01); *A61F 2220/0016* (2013.01); *A61F 2230/005* (2013.01); *A61F 2230/0054* (2013.01); *A61F 2250/0063* (2013.01)

(58) Field of Classification Search
USPC ............. 623/2.1, 2.11, 2.12, 2.17–2.19, 2.38, 623/2.4, 2.41
See application file for complete search history.

(56) References Cited

U.S. PATENT DOCUMENTS

| | | | |
|---|---|---|---|
| 4,261,342 A | 4/1981 | Aranguren Duo |
| 4,892,541 A | 1/1990 | Alonso |
| 5,108,420 A | 4/1992 | Marks |
| 5,607,444 A | 3/1997 | Lam |
| 5,607,470 A | 3/1997 | Milo |
| 5,868,777 A | 2/1999 | Lam |
| 6,042,607 A | 3/2000 | Williamson, IV et al. |
| 6,074,417 A | 6/2000 | Peredo |
| 6,113,612 A | 9/2000 | Swanson et al. |

(Continued)

FOREIGN PATENT DOCUMENTS

| | | |
|---|---|---|
| EP | 1264582 A2 | 12/2002 |
| WO | 99/30647 A1 | 6/1999 |

(Continued)

OTHER PUBLICATIONS

Alexander S. Geha, et al; "Replacement of Degenerated Mitral and Aortic Bioprostheses Without Explanation" Ann. Thorac Surg 2001; 72:1509-1514; Accepted for Publication Jun. 1, 2001.

(Continued)

*Primary Examiner* — Dianne Dornbusch
*Assistant Examiner* — Robert Lynch
(74) *Attorney, Agent, or Firm* — Ladas & Parry LLP

(57) ABSTRACT

Apparatus is provided, including one or more valve support guide members configured to be delivered to one or more commissures of a native atrioventricular valve of a patient, one or more valve support anchors configured to be anchored to the one or more commissures of the native valve, a prosthetic valve support advanceable toward the native valve along the one or more valve support guide members and anchored to the native valve at least the one or more commissures, and a prosthetic valve configured to be coupled to the valve support. Other applications are also described.

30 Claims, 13 Drawing Sheets

(56) References Cited

U.S. PATENT DOCUMENTS

| | | |
|---|---|---|
| 6,120,534 A | 9/2000 | Ruiz |
| 6,152,937 A | 11/2000 | Peterson et al. |
| 6,287,339 B1 | 9/2001 | Vazquez et al. |
| 6,332,893 B1 | 12/2001 | Mortier et al. |
| 6,391,036 B1 | 5/2002 | Berg et al. |
| 6,402,780 B2 | 6/2002 | Williamson, IV et al. |
| 6,409,755 B1 | 6/2002 | Vrba |
| 6,419,696 B1 | 7/2002 | Ortiz et al. |
| 6,428,550 B1 | 8/2002 | Vargas et al. |
| 6,440,164 B1 | 8/2002 | DiMatteo et al. |
| 6,458,153 B1 | 10/2002 | Bailey et al. |
| 6,511,491 B2 | 1/2003 | Grudem et al. |
| 6,530,952 B2 | 3/2003 | Vesely |
| 6,540,782 B1 | 4/2003 | Snyders |
| 6,558,418 B2 | 5/2003 | Carpentier et al. |
| 6,602,263 B1 | 8/2003 | Swanson et al. |
| 6,616,675 B1 | 9/2003 | Evard et al. |
| 6,699,256 B1 | 3/2004 | Logan et al. |
| 6,716,244 B2 | 4/2004 | Klaco |
| 6,719,781 B1 | 4/2004 | Kim |
| 6,730,118 B2 | 5/2004 | Spenser et al. |
| 6,767,362 B2 | 7/2004 | Schreck |
| 6,830,585 B1 | 12/2004 | Artof et al. |
| 6,830,638 B2 | 12/2004 | Boylan et al. |
| 6,960,217 B2 | 11/2005 | Bolduc |
| 6,964,684 B2 | 11/2005 | Ortiz et al. |
| 7,011,681 B2 | 3/2006 | Vesely |
| 7,018,406 B2 | 3/2006 | Seguin et al. |
| 7,041,132 B2 | 5/2006 | Quijano et al. |
| 7,077,861 B2 | 7/2006 | Spence |
| 7,101,395 B2 | 9/2006 | Tremulis et al. |
| 7,172,625 B2 | 2/2007 | Shu et al. |
| 7,198,646 B2 | 4/2007 | Figulla et al. |
| 7,201,772 B2 | 4/2007 | Schwammenthal et al. |
| 7,288,111 B1 | 10/2007 | Holloway et al. |
| 7,335,213 B1 | 2/2008 | Hyde et al. |
| 7,404,824 B1 | 7/2008 | Webler et al. |
| 7,422,603 B2 | 9/2008 | Lane |
| 7,429,269 B2 | 9/2008 | Schwammenthal et al. |
| 7,442,204 B2 | 10/2008 | Schwammenthal et al. |
| 7,455,677 B2 | 11/2008 | Vargas et al. |
| 7,455,688 B2 | 11/2008 | Furst et al. |
| 7,462,162 B2 | 12/2008 | Phan et al. |
| 7,481,838 B2 | 1/2009 | Carpentier et al. |
| 7,510,575 B2 | 3/2009 | Spenser et al. |
| 7,513,909 B2 | 4/2009 | Lane et al. |
| 7,527,646 B2 | 5/2009 | Rahdert et al. |
| 7,582,111 B2 | 9/2009 | Krolik et al. |
| 7,585,321 B2 | 9/2009 | Cribier |
| 7,632,302 B2 | 12/2009 | Vreeman et al. |
| 7,708,775 B2 | 5/2010 | Rowe et al. |
| 7,717,955 B2 | 5/2010 | Lane et al. |
| 7,731,741 B2 | 6/2010 | Eidenschink |
| 7,753,922 B2 | 7/2010 | Starksen |
| 7,771,467 B2 | 8/2010 | Svensson |
| 7,771,469 B2 | 8/2010 | Liddicoat |
| 7,780,726 B2 | 8/2010 | Seguin |
| 7,799,069 B2 | 9/2010 | Bailey et al. |
| 7,803,181 B2 | 9/2010 | Furst et al. |
| 7,837,727 B2 | 11/2010 | Goetz et al. |
| 7,842,081 B2 | 11/2010 | Yadin |
| 7,850,725 B2 | 12/2010 | Vardi et al. |
| 7,871,432 B2 | 1/2011 | Bergin |
| 7,871,436 B2 | 1/2011 | Ryan et al. |
| 7,887,583 B2 | 2/2011 | Macoviak |
| 7,892,281 B2 | 2/2011 | Seguin et al. |
| 7,896,915 B2 | 3/2011 | Guyenot et al. |
| 7,914,544 B2 | 3/2011 | Nguyen et al. |
| 7,914,569 B2 | 3/2011 | Nguyen et al. |
| 7,947,072 B2 | 5/2011 | Yang et al. |
| 7,947,075 B2 | 5/2011 | Goetz et al. |
| 7,955,375 B2 | 6/2011 | Agnew |
| 7,955,384 B2 | 6/2011 | Rafiee et al. |
| 7,967,833 B2 | 6/2011 | Sterman et al. |
| 7,967,857 B2 | 6/2011 | Lane |
| 7,981,151 B2 | 7/2011 | Rowe |
| 7,981,153 B2 | 7/2011 | Fogarty et al. |
| 7,992,567 B2 * | 8/2011 | Hirotsuka et al. ............ 128/848 |
| 7,993,393 B2 | 8/2011 | Carpentier et al. |
| 8,002,825 B2 | 8/2011 | Letac et al. |
| 8,016,877 B2 | 9/2011 | Seguin et al. |
| 8,016,882 B2 | 9/2011 | Macoviak et al. |
| 8,021,420 B2 | 9/2011 | Dolan |
| 8,021,421 B2 | 9/2011 | Fogarty et al. |
| 8,029,564 B2 | 10/2011 | Johnson et al. |
| 8,034,104 B2 | 10/2011 | Carpentier et al. |
| 8,043,360 B2 | 10/2011 | McNamara et al. |
| 8,048,140 B2 | 11/2011 | Purdy |
| 8,048,153 B2 | 11/2011 | Salahieh et al. |
| 8,052,741 B2 | 11/2011 | Bruszewski et al. |
| 8,057,532 B2 | 11/2011 | Hoffman |
| 8,057,540 B2 | 11/2011 | Letac et al. |
| 8,062,355 B2 | 11/2011 | Figulla et al. |
| 8,062,359 B2 | 11/2011 | Marquez et al. |
| 8,070,708 B2 | 12/2011 | Rottenberg et al. |
| 8,070,802 B2 | 12/2011 | Lamphere et al. |
| 8,070,804 B2 | 12/2011 | Hyde et al. |
| 8,075,611 B2 | 12/2011 | Millwee et al. |
| 8,080,054 B2 | 12/2011 | Rowe |
| 8,092,518 B2 | 1/2012 | Schreck |
| 8,092,520 B2 | 1/2012 | Quadri |
| 8,092,521 B2 | 1/2012 | Figulla et al. |
| 8,105,377 B2 | 1/2012 | Liddicoat |
| 8,118,866 B2 | 2/2012 | Herrmann et al. |
| 8,136,218 B2 | 3/2012 | Millwee et al. |
| 8,137,398 B2 | 3/2012 | Tuval et al. |
| 8,142,492 B2 | 3/2012 | Forster et al. |
| 8,142,494 B2 | 3/2012 | Rahdert et al. |
| 8,142,496 B2 | 3/2012 | Berreklouw |
| 8,142,497 B2 | 3/2012 | Friedman |
| 8,147,504 B2 | 4/2012 | Ino et al. |
| 8,157,852 B2 | 4/2012 | Bloom et al. |
| 8,157,853 B2 | 4/2012 | Laske et al. |
| 8,157,860 B2 | 4/2012 | McNamara et al. |
| 8,163,014 B2 | 4/2012 | Lane et al. |
| 8,167,894 B2 | 5/2012 | Miles et al. |
| 8,167,932 B2 | 5/2012 | Bourang et al. |
| 8,172,896 B2 | 5/2012 | McNamara et al. |
| 8,177,836 B2 | 5/2012 | Lee et al. |
| 8,182,528 B2 | 5/2012 | Salahieh et al. |
| 8,211,169 B2 | 7/2012 | Lane et al. |
| 8,221,492 B2 | 7/2012 | Case et al. |
| 8,221,493 B2 | 7/2012 | Boyle et al. |
| 8,226,710 B2 | 7/2012 | Nguyen et al. |
| 8,231,670 B2 | 7/2012 | Salahieh et al. |
| 8,236,045 B2 | 8/2012 | Benichou et al. |
| 8,236,049 B2 | 8/2012 | Rowe et al. |
| 8,252,042 B2 | 8/2012 | McNamara et al. |
| 8,252,051 B2 | 8/2012 | Chau et al. |
| 8,252,052 B2 | 8/2012 | Salahieh et al. |
| 8,257,390 B2 | 9/2012 | Carley et al. |
| 8,277,501 B2 | 10/2012 | Chalekian et al. |
| 8,287,591 B2 | 10/2012 | Keidar et al. |
| 8,298,280 B2 | 10/2012 | Yadin et al. |
| 8,308,798 B2 | 11/2012 | Pintor et al. |
| 8,317,853 B2 | 11/2012 | Agnew |
| 8,317,855 B2 | 11/2012 | Gregorich et al. |
| 8,323,335 B2 | 12/2012 | Rowe et al. |
| 8,328,868 B2 | 12/2012 | Paul et al. |
| 8,343,174 B2 | 1/2013 | Goldfarb et al. |
| 8,430,934 B2 | 4/2013 | Das |
| 8,449,625 B2 | 5/2013 | Campbell et al. |
| 8,696,742 B2 | 4/2014 | Pintor et al. |
| 2001/0021872 A1 | 9/2001 | Bailey et al. |
| 2002/0151970 A1 * | 10/2002 | Garrison et al. ............ 623/2.11 |
| 2003/0036791 A1 | 2/2003 | Philipp et al. |
| 2003/0074052 A1 | 4/2003 | Besselink |
| 2003/0083742 A1 | 5/2003 | Spence et al. |
| 2003/0105519 A1 | 6/2003 | Fasol et al. |
| 2003/0158578 A1 | 8/2003 | Pantages et al. |
| 2004/0039414 A1 | 2/2004 | Carley et al. |
| 2004/0093060 A1 | 5/2004 | Seguin et al. |
| 2004/0122514 A1 | 6/2004 | Fogarty et al. |
| 2004/0176839 A1 * | 9/2004 | Huynh et al. ................ 623/2.4 |

(56) References Cited

U.S. PATENT DOCUMENTS

| | | |
|---|---|---|
| 2004/0186565 A1 | 9/2004 | Schreck |
| 2004/0186566 A1 | 9/2004 | Hindrichs et al. |
| 2004/0210244 A1 | 10/2004 | Vargas et al. |
| 2004/0225354 A1 | 11/2004 | Allen et al. |
| 2004/0260389 A1 | 12/2004 | Case et al. |
| 2005/0004668 A1 | 1/2005 | Aklog et al. |
| 2005/0075731 A1 | 4/2005 | Artof et al. |
| 2005/0137688 A1 | 6/2005 | Salahieh et al. |
| 2005/0137689 A1 | 6/2005 | Salahieh et al. |
| 2005/0137690 A1 | 6/2005 | Salahieh et al. |
| 2005/0137695 A1 | 6/2005 | Salahieh et al. |
| 2005/0143809 A1 | 6/2005 | Salahieh et al. |
| 2005/0197695 A1 | 9/2005 | Stacchino et al. |
| 2005/0203549 A1 | 9/2005 | Realyvasquez |
| 2005/0216079 A1* | 9/2005 | MaCoviak .................. 623/2.38 |
| 2005/0234508 A1 | 10/2005 | Cummins et al. |
| 2005/0240200 A1 | 10/2005 | Bergheim |
| 2005/0251251 A1 | 11/2005 | Cribier |
| 2005/0267573 A9 | 12/2005 | Macoviak et al. |
| 2006/0047297 A1 | 3/2006 | Case |
| 2006/0135964 A1 | 6/2006 | Vesely |
| 2006/0178740 A1 | 8/2006 | Stacchino et al. |
| 2006/0190036 A1 | 8/2006 | Wendel et al. |
| 2006/0190038 A1 | 8/2006 | Carley et al. |
| 2006/0195184 A1* | 8/2006 | Lane et al. .................. 623/2.38 |
| 2006/0201519 A1 | 9/2006 | Frazier et al. |
| 2006/0241656 A1 | 10/2006 | Starksen et al. |
| 2006/0241748 A1 | 10/2006 | Lee et al. |
| 2006/0247680 A1 | 11/2006 | Amplatz et al. |
| 2006/0253191 A1 | 11/2006 | Salahieh et al. |
| 2006/0259136 A1 | 11/2006 | Nguyen et al. |
| 2006/0271166 A1 | 11/2006 | Thill et al. |
| 2006/0271171 A1 | 11/2006 | McQuinn et al. |
| 2007/0016288 A1 | 1/2007 | Gurskis et al. |
| 2007/0038295 A1 | 2/2007 | Case et al. |
| 2007/0043435 A1 | 2/2007 | Seguin et al. |
| 2007/0112422 A1 | 5/2007 | Dehdashtian |
| 2007/0118151 A1 | 5/2007 | Davidson |
| 2007/0162103 A1 | 7/2007 | Case et al. |
| 2007/0162107 A1 | 7/2007 | Haug et al. |
| 2007/0162111 A1 | 7/2007 | Fukamachi et al. |
| 2007/0173932 A1 | 7/2007 | Cali et al. |
| 2007/0198097 A1 | 8/2007 | Zegdi |
| 2007/0213813 A1 | 9/2007 | Von Segesser et al. |
| 2007/0225759 A1 | 9/2007 | Thommen et al. |
| 2007/0225760 A1 | 9/2007 | Moszner et al. |
| 2007/0233186 A1 | 10/2007 | Meng |
| 2007/0233237 A1 | 10/2007 | Krivoruchko |
| 2007/0239272 A1 | 10/2007 | Navia et al. |
| 2007/0255400 A1 | 11/2007 | Parravicini et al. |
| 2008/0004688 A1 | 1/2008 | Spenser et al. |
| 2008/0004697 A1 | 1/2008 | Lichtenstein et al. |
| 2008/0071363 A1 | 3/2008 | Tuval et al. |
| 2008/0071366 A1 | 3/2008 | Tuval et al. |
| 2008/0071369 A1 | 3/2008 | Tuval et al. |
| 2008/0077235 A1 | 3/2008 | Kirson |
| 2008/0086164 A1* | 4/2008 | Rowe ............................ 606/191 |
| 2008/0086204 A1 | 4/2008 | Rankin |
| 2008/0161910 A1 | 7/2008 | Revuelta et al. |
| 2008/0167714 A1* | 7/2008 | St. Goar et al. .............. 623/2.11 |
| 2008/0195200 A1 | 8/2008 | Vidlund et al. |
| 2008/0208332 A1 | 8/2008 | Lamphere et al. |
| 2008/0221672 A1 | 9/2008 | Lamphere et al. |
| 2008/0243245 A1 | 10/2008 | Thambar et al. |
| 2008/0262609 A1 | 10/2008 | Gross et al. |
| 2008/0281411 A1* | 11/2008 | Berreklouw .................. 623/2.11 |
| 2009/0005863 A1 | 1/2009 | Goetz et al. |
| 2009/0054969 A1 | 2/2009 | Salahieh et al. |
| 2009/0099650 A1 | 4/2009 | Bolduc et al. |
| 2009/0177278 A1 | 7/2009 | Spence |
| 2009/0210052 A1 | 8/2009 | Forster et al. |
| 2009/0264994 A1 | 10/2009 | Saadat |
| 2009/0287304 A1 | 11/2009 | Dahlgren et al. |
| 2009/0319037 A1 | 12/2009 | Rowe et al. |
| 2010/0023117 A1 | 1/2010 | Yoganathan et al. |
| 2010/0036479 A1 | 2/2010 | Hill et al. |
| 2010/0076548 A1 | 3/2010 | Konno |
| 2010/0114299 A1 | 5/2010 | Ben Muvhar et al. |
| 2010/0131054 A1 | 5/2010 | Tuval et al. |
| 2010/0137979 A1 | 6/2010 | Tuval et al. |
| 2010/0160958 A1 | 6/2010 | Clark |
| 2010/0161036 A1 | 6/2010 | Pintor et al. |
| 2010/0161042 A1 | 6/2010 | Maisano et al. |
| 2010/0174363 A1 | 7/2010 | Castro |
| 2010/0179643 A1 | 7/2010 | Shalev |
| 2010/0179648 A1 | 7/2010 | Richter et al. |
| 2010/0179649 A1 | 7/2010 | Richter et al. |
| 2010/0217382 A1 | 8/2010 | Chau et al. |
| 2010/0222810 A1 | 9/2010 | DeBeer et al. |
| 2010/0228285 A1 | 9/2010 | Miles et al. |
| 2010/0234940 A1 | 9/2010 | Dolan |
| 2010/0249908 A1 | 9/2010 | Chau et al. |
| 2010/0249917 A1 | 9/2010 | Zhang |
| 2010/0262232 A1 | 10/2010 | Annest |
| 2010/0280606 A1 | 11/2010 | Naor |
| 2010/0324595 A1 | 12/2010 | Linder et al. |
| 2011/0004296 A1 | 1/2011 | Lutter et al. |
| 2011/0015729 A1 | 1/2011 | Jimenez et al. |
| 2011/0015731 A1 | 1/2011 | Carpentier et al. |
| 2011/0022165 A1 | 1/2011 | Oba et al. |
| 2011/0040374 A1 | 2/2011 | Goetz et al. |
| 2011/0040375 A1 | 2/2011 | Letac et al. |
| 2011/0046662 A1 | 2/2011 | Moszner et al. |
| 2011/0054466 A1 | 3/2011 | Rothstein et al. |
| 2011/0054596 A1 | 3/2011 | Taylor |
| 2011/0054598 A1 | 3/2011 | Johnson |
| 2011/0082538 A1* | 4/2011 | Dahlgren et al. ............ 623/2.11 |
| 2011/0087322 A1 | 4/2011 | Letac et al. |
| 2011/0093063 A1 | 4/2011 | Schreck |
| 2011/0106247 A1* | 5/2011 | Miller et al. ................. 623/2.17 |
| 2011/0112625 A1 | 5/2011 | Ben-Muvhar et al. |
| 2011/0112632 A1 | 5/2011 | Chau et al. |
| 2011/0118830 A1 | 5/2011 | Liddicoat et al. |
| 2011/0125257 A1 | 5/2011 | Seguin et al. |
| 2011/0125258 A1 | 5/2011 | Centola |
| 2011/0137326 A1 | 6/2011 | Bachman |
| 2011/0137397 A1 | 6/2011 | Chau et al. |
| 2011/0137409 A1 | 6/2011 | Yang et al. |
| 2011/0137410 A1 | 6/2011 | Hacohen |
| 2011/0166636 A1 | 7/2011 | Rowe |
| 2011/0172784 A1 | 7/2011 | Richter et al. |
| 2011/0178597 A9 | 7/2011 | Navia et al. |
| 2011/0190877 A1 | 8/2011 | Lane et al. |
| 2011/0190879 A1 | 8/2011 | Bobo et al. |
| 2011/0202076 A1 | 8/2011 | Richter |
| 2011/0208283 A1* | 8/2011 | Rust ............................. 623/1.11 |
| 2011/0208293 A1 | 8/2011 | Tabor |
| 2011/0208298 A1 | 8/2011 | Tuval et al. |
| 2011/0213461 A1 | 9/2011 | Seguin et al. |
| 2011/0218619 A1 | 9/2011 | Benichou et al. |
| 2011/0218620 A1 | 9/2011 | Meiri et al. |
| 2011/0224785 A1 | 9/2011 | Hacohen |
| 2011/0245911 A1 | 10/2011 | Quill et al. |
| 2011/0245917 A1 | 10/2011 | Savage et al. |
| 2011/0251675 A1 | 10/2011 | Dwork |
| 2011/0251676 A1 | 10/2011 | Sweeney et al. |
| 2011/0251679 A1 | 10/2011 | Wiemeyer et al. |
| 2011/0251680 A1 | 10/2011 | Tran et al. |
| 2011/0251682 A1 | 10/2011 | Murray, III et al. |
| 2011/0251683 A1 | 10/2011 | Tabor |
| 2011/0257721 A1 | 10/2011 | Tabor |
| 2011/0257729 A1 | 10/2011 | Spenser et al. |
| 2011/0257736 A1 | 10/2011 | Marquez et al. |
| 2011/0257737 A1 | 10/2011 | Fogarty et al. |
| 2011/0264191 A1 | 10/2011 | Rothstein |
| 2011/0264196 A1 | 10/2011 | Savage et al. |
| 2011/0264198 A1 | 10/2011 | Murray, III et al. |
| 2011/0264199 A1 | 10/2011 | Tran et al. |
| 2011/0264200 A1 | 10/2011 | Tran et al. |
| 2011/0264201 A1 | 10/2011 | Yeung et al. |
| 2011/0264202 A1 | 10/2011 | Murray, III et al. |
| 2011/0264203 A1 | 10/2011 | Dwork et al. |
| 2011/0264206 A1 | 10/2011 | Tabor |
| 2011/0264208 A1 | 10/2011 | Duffy et al. |

(56) References Cited

U.S. PATENT DOCUMENTS

| | | |
|---|---|---|
| 2011/0270276 A1 | 11/2011 | Rothstein et al. |
| 2011/0271967 A1 | 11/2011 | Mortier et al. |
| 2011/0282438 A1 | 11/2011 | Drews et al. |
| 2011/0283514 A1 | 11/2011 | Fogarty et al. |
| 2011/0288634 A1 | 11/2011 | Tuval et al. |
| 2011/0301688 A1 | 12/2011 | Dolan |
| 2011/0301702 A1 | 12/2011 | Rust et al. |
| 2011/0313452 A1 | 12/2011 | Carley et al. |
| 2011/0319989 A1 | 12/2011 | Lane |
| 2011/0319991 A1 | 12/2011 | Hariton et al. |
| 2012/0010694 A1 | 1/2012 | Lutter et al. |
| 2012/0022633 A1 | 1/2012 | Olson et al. |
| 2012/0022637 A1 | 1/2012 | Ben-Muvhar |
| 2012/0022639 A1 | 1/2012 | Hacohen et al. |
| 2012/0022640 A1 | 1/2012 | Gross et al. |
| 2012/0035703 A1 | 2/2012 | Lutter et al. |
| 2012/0035713 A1 | 2/2012 | Lutter et al. |
| 2012/0035722 A1 | 2/2012 | Tuval |
| 2012/0041547 A1 | 2/2012 | Duffy et al. |
| 2012/0041551 A1 | 2/2012 | Spenser et al. |
| 2012/0046738 A1 | 2/2012 | Lau et al. |
| 2012/0046742 A1 | 2/2012 | Tuval et al. |
| 2012/0053682 A1 | 3/2012 | Kovalsky et al. |
| 2012/0053688 A1 | 3/2012 | Fogarty et al. |
| 2012/0059454 A1 | 3/2012 | Millwee et al. |
| 2012/0078353 A1 | 3/2012 | Quadri et al. |
| 2012/0078357 A1 | 3/2012 | Conklin |
| 2012/0083832 A1 | 4/2012 | Delaloye et al. |
| 2012/0083839 A1 | 4/2012 | Letac et al. |
| 2012/0083879 A1 | 4/2012 | Eberhardt et al. |
| 2012/0089223 A1 | 4/2012 | Nguyen et al. |
| 2012/0101570 A1 | 4/2012 | Tuval et al. |
| 2012/0101572 A1 | 4/2012 | Kovalsky et al. |
| 2012/0123530 A1 | 5/2012 | Carpentier et al. |
| 2012/0136434 A1 | 5/2012 | Carpentier et al. |
| 2012/0150218 A1 | 6/2012 | Sandgren et al. |
| 2012/0197292 A1 | 8/2012 | Chin-Chen et al. |
| 2012/0283824 A1 | 11/2012 | Lutter et al. |
| 2012/0290062 A1 | 11/2012 | McNamara et al. |
| 2012/0310328 A1 | 12/2012 | Olson et al. |
| 2012/0323316 A1 | 12/2012 | Chau et al. |
| 2013/0035759 A1 | 2/2013 | Gross et al. |
| 2013/0261737 A1 | 10/2013 | Costello |
| 2013/0304197 A1 | 11/2013 | Buchbinder et al. |
| 2013/0325114 A1 | 12/2013 | McLean et al. |
| 2014/0005778 A1 | 1/2014 | Buchbinder et al. |
| 2014/0052237 A1 | 2/2014 | Lane et al. |

FOREIGN PATENT DOCUMENTS

| | | |
|---|---|---|
| WO | 00/47139 A1 | 8/2000 |
| WO | 01/62189 A1 | 8/2001 |
| WO | 2006/054930 A1 | 5/2006 |
| WO | 2008/013915 A3 | 1/2008 |
| WO | 2009/033469 A1 | 3/2009 |
| WO | 2009/053497 A1 | 4/2009 |
| WO | 2010/006627 A1 | 1/2010 |
| WO | 2010/073246 A2 | 7/2010 |
| WO | 2011/106137 A1 | 9/2011 |
| WO | 2011/111047 A2 | 9/2011 |
| WO | 2011/143263 A2 | 11/2011 |
| WO | 2012/011108 A2 | 1/2012 |
| WO | 2013/021374 A2 | 2/2013 |
| WO | 2013/021375 A2 | 2/2013 |
| WO | 2013/078497 A1 | 6/2013 |
| WO | 2013/128436 A1 | 9/2013 |

OTHER PUBLICATIONS

John G. Webb, et al; "Transcatheter Valve-in-Valve Implantation for Failed Bioprosthetic Heart Valves", Circulation 2010; 121; 1848-1857, originally published online Apr. 12, 2010.

International Search Report; mailed Oct. 13, 2011; PCT/IL11/00231.

Frank Langer, et al; "RING plus STRING: Papillary muscle repositioning as an adjunctive repair technique for ischemic mitral regurgitation", J. Thorac Cardiovasc Surg 133: 247-9 (2007).

Frank Lanfer, et al; "RING + STRING Successful Repair Technique for Ischemic Mitral Regurgitation With Severe Leaflet Tethering", Circulation 120[suppl 1]: S85-S91, (2009).

John G. Webb, et al; "Transcatheter Valve-in-Valve Implantation for Failed Bioprosthetic Heart Valves", Circulation, Apr. 27, 2010, vol. 121, No. 16, pp. 1848-1857.

J. Jansen, et al; "Detachable shape-memory sewing ring for heart valves" Artificial Organs, vol. 16, Issue 3, pp. 294-297, Jun. 1992.

Alexander S. Geha, et el; "Replacement of Degenerated Mitral and Aortic Boprostheses Without Explantation", The Annuals of Thoracic Surgery, vol. 72, Issue 5, Nov. 2001, pp. 1509-1514.

International Search Report and Written Opinion dated Dec. 5, 2011, issued during prosecution of PCT/IL11/00582.

USPTO NFOA dated Nov. 28, 2012 in connection with U.S. Appl. No. 12/961,721.

USPTO NFOA dated Nov. 23, 2012 in connection with U.S. Appl. No. 13/033,852.

USPTO NFOA dated Dec. 31, 2012 in connection with U.S. Appl. No. 13/044,694.

USPTO NFOA dated Feb. 6, 2013 in connection with U.S. Appl. No. 13/412,814.

International Search Report and Written Opinion dated Feb. 6, 2013 PCT/IL12/00292.

International Search Report and Written Opinion dated Feb. 6, 2013 PCT/IL12/00293.

An Office Action dated Jul. 18, 2013, which issued during the prosecution of U.S. Appl. No. 13/044,694.

An Office Action dated Aug. 2, 2013, which issued during the prosecution of U.S. Appl. No. 13/033,852.

USPTO NFOA dated Sep. 12, 2013 in connection with U.S. Appl. No. 13/412,814.

International Preliminary Report on Patentability dated Dec. 2, 2013; PCT/IL11/00582.

USPTO NFOA dated Jul. 3, 2014 in connection with U.S. Appl. No. 13/033,852.

USPTO FOA dated May 23, 2014 in connection with U.S. Appl. No. 13/412,814.

USPTO NFOA dated Jul. 2, 2014 in connection with U.S. Appl. No. 13/811,308.

Invitation to Pay Additional Fees dted Jun. 12, 2014; PCT/IL2014/050087.

International Search Report and Written Opinion dated Sep. 4, 2014; PCT/IL2014/050087.

USPTO NFOA dated Sep. 19, 2014 in connection with U.S. Appl. No. 13/044,694.

\* cited by examiner

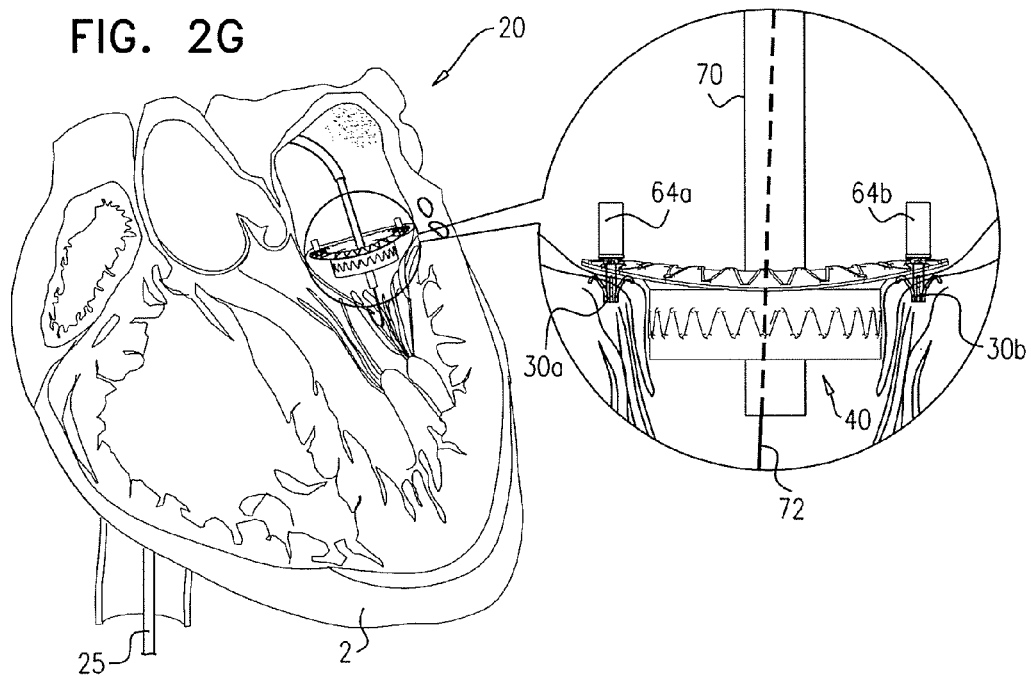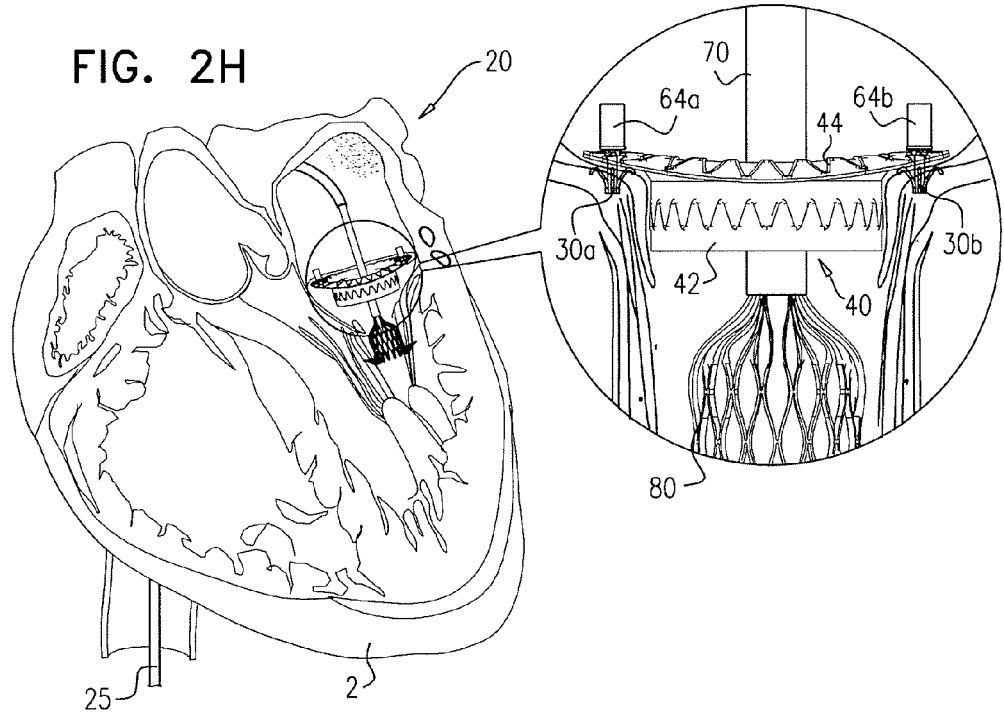

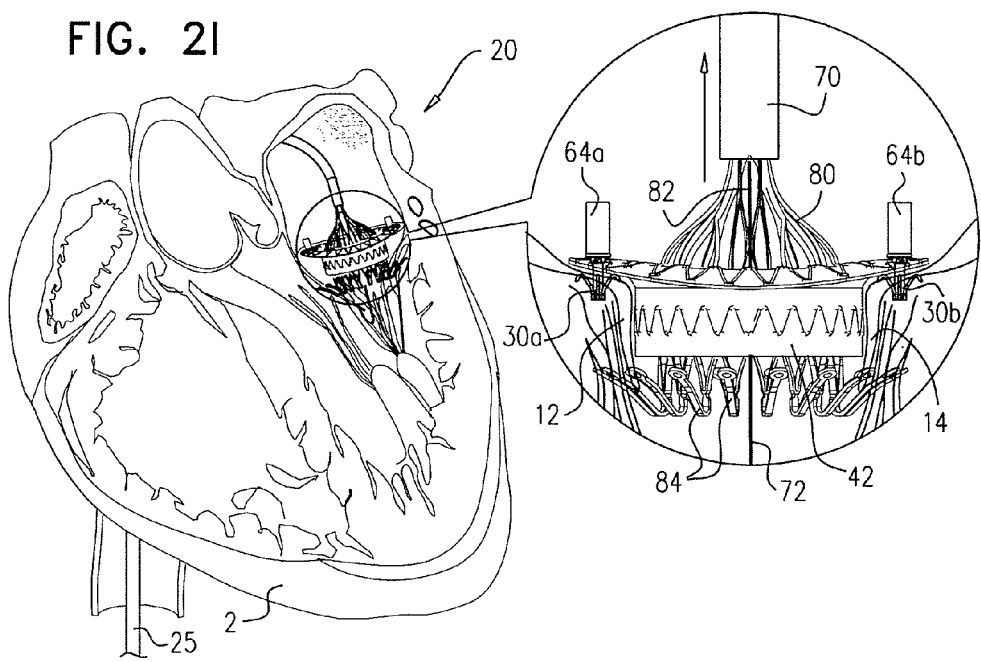
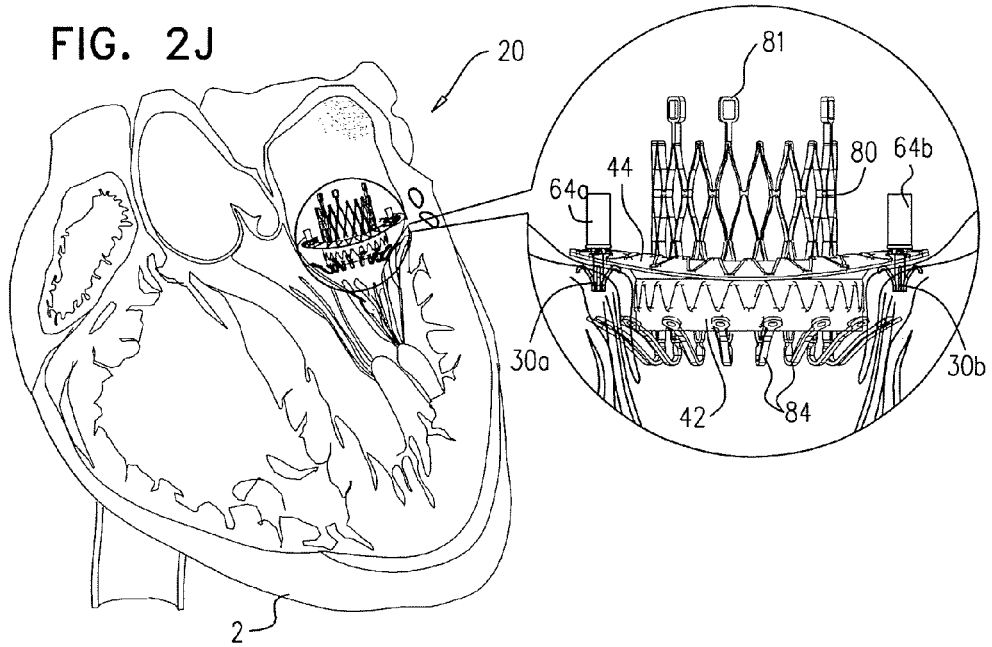

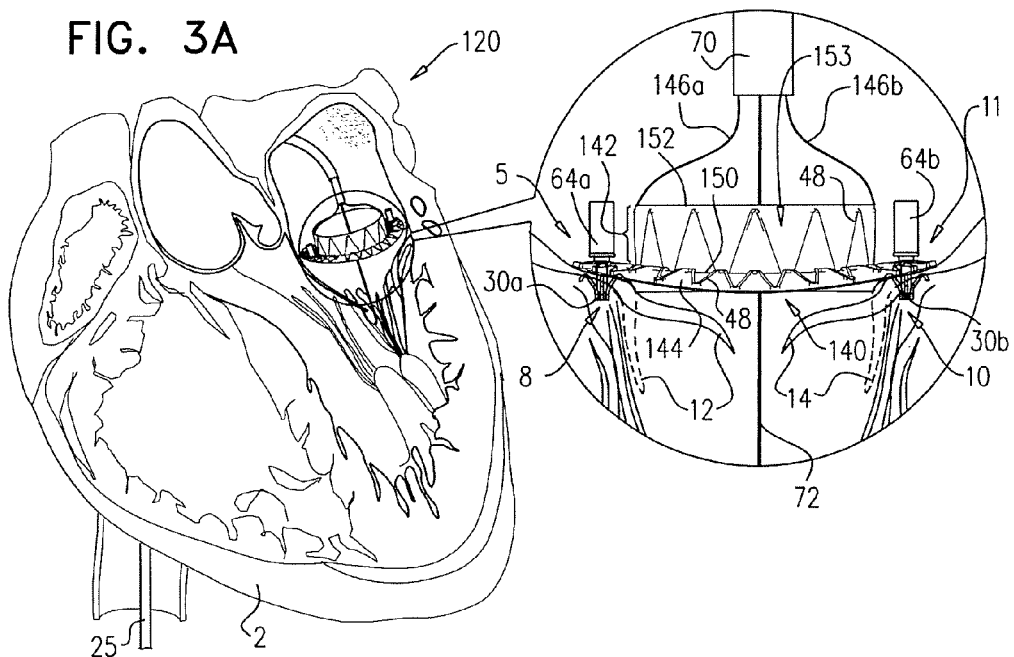
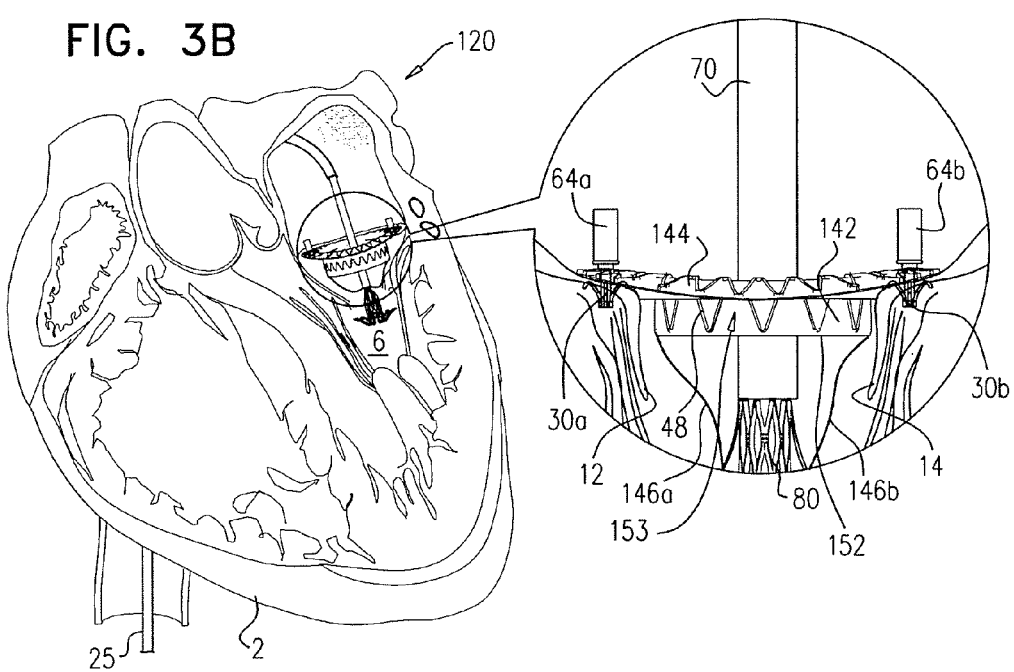

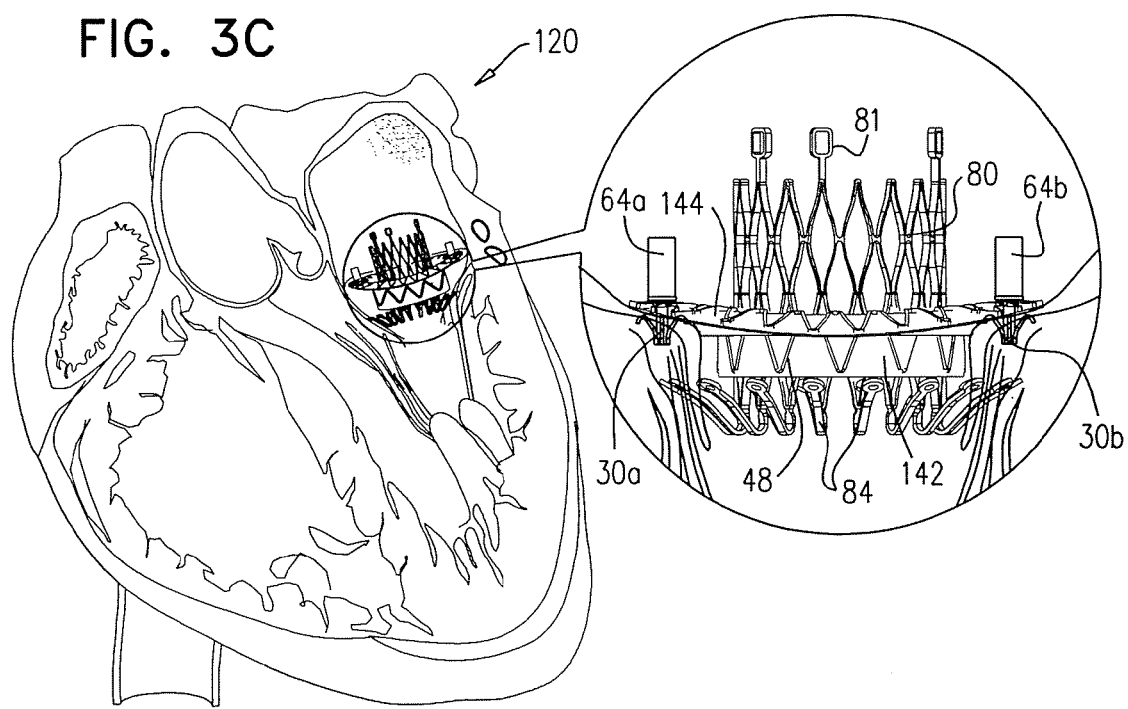

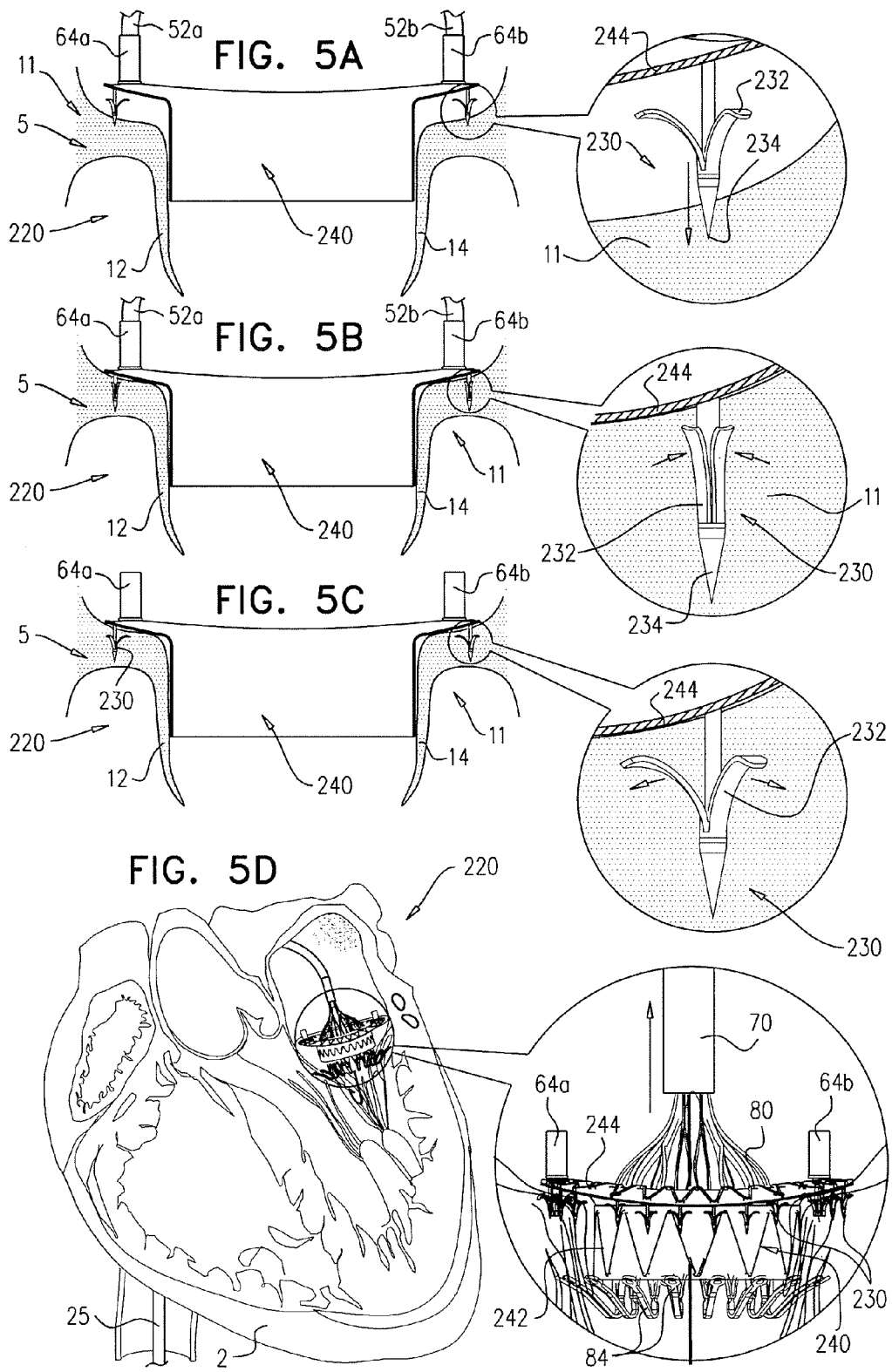

GUIDE WIRES WITH COMMISSURAL ANCHORS TO ADVANCE A PROSTHETIC VALVE

FIELD OF THE INVENTION

Embodiments of the present invention relate in general to valve replacement. More specifically, embodiments of the present invention relate to prosthetic valves for replacement of an atrioventricular valve.

BACKGROUND

Ischemic heart disease causes regurgitation of a heart valve by the combination of ischemic dysfunction of the papillary muscles, and the dilatation of the ventricle that is present in ischemic heart disease, with the subsequent displacement of the papillary muscles and the dilatation of the valve annulus.

Dilation of the annulus of the valve prevents the valve leaflets from fully coapting when the valve is closed. Regurgitation of blood from the ventricle into the atrium results in increased total stroke volume and decreased cardiac output, and ultimate weakening of the ventricle secondary to a volume overload and a pressure overload of the atrium.

PCT Publication WO 09/033,469 to Lutter et al. describes a heart valve stent having a section equipped to receive a heart valve implant and a plurality of proximally disposed anchoring elements, characterized by a plurality of anchoring threads, which with the one end thereof are fastened to the stent, and further having a brace fastening the anchoring threads with the other end thereof to the distal chamber wall to provide tension between the heart chamber wall and the proximally anchored anchoring elements.

U.S. Pat. No. 7,018,406 to Seguin et al. describes a prosthetic valve assembly for use in replacing a deficient native valve comprising a replacement valve supported on an expandable valve support. If desired, one or more anchors may be used. The valve support, which is described as entirely supporting the valve annulus, valve leaflets, and valve commissure points, is configured to be collapsible for transluminal delivery and expandable to contact the anatomical annulus of the native valve when the assembly is properly positioned. The anchor engages the lumen wall when expanded and prevents substantial migration of the valve assembly when positioned in place. The prosthetic valve assembly is compressible about a catheter, and restrained from expanding by an outer sheath. The catheter may be inserted inside a lumen within the body, such as the femoral artery, and delivered to a desired location, such as the heart. When the outer sheath is retracted, the prosthetic valve assembly expands to an expanded position such that the valve and valve support expand within the deficient native valve, and the anchor engages the lumen wall.

US Patent Application Publication 2007/0213813 to Von Segesser et al. describes stent-valves (e.g., single-stent-valves and double-stent-valves), associated methods and systems for their delivery via minimally-invasive surgery, and guide-wire compatible closure devices for sealing access orifices are provided.

US Patent Application Publication 2008/0208332 to Lamphere et al. describes valve prostheses that are adapted for secure and aligned placement relative to a heart annulus. The valve prostheses may be placed in a non-invasive manner, e.g., via trans-catheter techniques, and may be positioned/repositioned until proper alignment and positioning is achieved. The valve prosthesis may include a resilient ring, a plurality of leaflet membranes mounted with respect to the resilient ring, and a plurality of positioning elements movably mounted with respect to the flexible ring, each of the positioning elements defining a first tissue engaging region and a second tissue engaging region spaced from the first tissue engaging region. The positioning elements are adapted to substantially completely invert by rotating relative to the resilient ring between a first position in which each of the first and second tissue engaging regions is inwardly directed for facilitating positioning of the valve prosthesis within a delivery catheter, and a second position in which each of the first and second tissue engaging regions is outwardly directed for engaging tissue. The valve prosthesis may also include a valve skirt mounted with respect to the resilient ring.

U.S. Pat. No. 6,458,153 to Bailey et al. describes prosthetic cardiac and venous valves and a single catheter device and minimally invasive techniques for percutaneous and transluminal valvuloplasty and prosthetic valve implantation.

U.S. Pat. No. 6,767,362 to Schreck describes expandable heart valves for minimally invasive valve replacement surgeries. In a first embodiment, an expandable pre-assembled heart valve includes a plastically-expandable annular base having plurality of upstanding commissure posts. A tubular flexible member including a prosthetic section and a fabric section is provided, with the prosthetic section being connected to the commissure posts and defining leaflets therebetween, and the fabric section being attached to the annular base. In a second embodiment, an expandable heart valve includes an annular tissue-engaging base and a subassembly having an elastic wireform and a plurality of leaflets connected thereto. The annular base and subassembly are separately stored and connected just prior to delivery to the host annulus. Preferably, the leaflet subassembly is stored in its relaxed configuration to avoid deformation of the leaflets. The expandable heart valves may be implanted using a balloon catheter. Preferably, the leaflets of the heart valves are secured to the commissure regions of the expandable stents using a clamping arrangement to reduce stress.

U.S. Pat. No. 7,481,838 to Carpentier et al. describes a highly flexible tissue-type heart valve having a structural stent in a generally cylindrical configuration with cusps and commissures that are permitted to move radially. The stent commissures are constructed so that the cusps are pivotably or flexibly coupled together at the commissures to permit relative movement therebetween.

US Patent Application Publication 2009/0210052 to Forster et al. describes systems and methods for operation of a prosthetic valve support structure having additional reinforcement coupled with panels. Multiple support members are distributed across the inner surface of the valve support structure at regular intervals. Each support member can include a looped portion to act as a hinge. Each looped portion is in a location coincidental with the interlace between adjacent panels.

The following references may be of interest:

U.S. Pat. No. 4,261,342 to Aranguren Duo
U.S. Pat. No. 6,074,417 to Peredo
U.S. Pat. No. 6,332,893 to Mortier et al.
U.S. Pat. No. 7,101,395 to Tremulis et al.
U.S. Pat. No. 7,404,824 to Webler et al.
US Patent Application Publication 2003/0105519 to Fasol et al.
US Patent Application Publication 2005/0004668 to Aklog et al.
US Patent Application Publication 2005/0137688 to Salahieh et al.
US Patent Application Publication 2006/0253191 to Salahieh et al. doc US Patent Application Publication 2008/0243245 to Thambar et al.

US Patent Application Publication 2008/0262609 to Gross et al.

US Patent Application Publication 2009/0177278 to Spence

PCT Publication WO 06/054930 to Antonsson et al.

PCT Publication WO 08/013,915 to Quadri

PCT Publication WO 09/053,497 to Essinger et al.

Langer F et al., "RING plus STRING: Papillary muscle repositioning as an adjunctive repair technique for ischemic mitral regurgitation," J Thorac Cardiovasc Surg 133:247-9 (2007)

Langer F et al., "RING+STRING: Successful repair technique for ischemic mitral regurgitation with severe leaflet tethering," Circulation 120[suppl 1]:S85-S91 (2009)

SUMMARY OF EMBODIMENTS

In some embodiments of the present invention, one or more guide members (e.g., wires, sutures, or strings) is configured to be anchored to respective commissures of a native atrioventricular valve of a patient, and each guide member facilitates the advancement therealong of respective commissural anchors. The commissural anchors are shaped so as to define a plurality of barbs or prongs which are expandable to restrict proximal movement of the anchors following their deployment. The guide members facilitate advancement of a collapsible prosthetic valve support (e.g., a skirt) which serves as a base for and receives a collapsible prosthetic mitral valve which is subsequently coupled to the support. The support comprises a proximal annular element, or ring, and a distal cylindrical element. The cylindrical element is configured to push aside and press against the native leaflets of the native valve, and the proximal annular element is shaped so as to define one or more holes for sliding the valve support along the one or more guide members. The proximal annular element is configured to be positioned along the annulus of the native valve.

The collapsible prosthetic valve is configured for implantation in and/or at least partial replacement (e.g., full replacement) of the native atrioventricular valve of the patient, such as a native mitral valve or a native tricuspid valve. The valve support and the prosthetic valve are configured to assume collapsed states for minimally-invasive delivery to the diseased native valve, such as by percutaneous or transluminal delivery using one or more catheters. For some applications, the valve support and the prosthetic valve are implanted during an open-heart procedure.

The prosthetic valve support is shaped so as to define a downstream skirt. The downstream skirt is configured to be placed at native valve, such that the downstream skirt passes through the orifice of the native valve and extends toward, and, typically partially into, a ventricle. The downstream skirt typically additionally pushes aside and presses against the native leaflets of the native valve, which are left in place during and after implantation of the prosthetic valve support and/or the prosthetic valve.

The proximal annular element has upper and lower surfaces. For some applications of the present invention, one or more, e.g., a plurality of tissue anchors are coupled to the lower surface and facilitate anchoring of the proximal annular element to the annulus of the native valve. For some applications, the one or more anchors comprise at least first and second commissural anchors that are configured to be implanted at or in the vicinity of the commissures of the native valve.

The cylindrical element of the valve support has first and second ends and a cylindrical body disposed between the first and second ends. The first end of the cylindrical element is coupled to the annular element while the second end defines a free end of the cylindrical element. For some applications of the present invention, the cylindrical element of the valve support is invertible such that (1) during a first period, the second end and the cylindrical body of the cylindrical element are disposed above the annular element (e.g., in the atrium of the heart), and (2) during a second period, the second end and the cylindrical body of the cylindrical element are disposed below the annular element (e.g., in the ventricle of the heart).

There is therefore provided, in accordance with some applications of the present invention, apparatus, including:

one or more valve support guide members configured to be delivered to one or more commissures of a native atrioventricular valve of a patient;

one or more valve support anchors configured to be anchored to the one or more commissures of the native valve;

a prosthetic valve support advanceable toward the native valve along the one or more valve support guide members and anchored to the native valve at least the one or more commissures; and a prosthetic valve configured to be coupled to the valve support.

In some applications of the present invention, the valve support is collapsible for transcatheter delivery and expandable to contact the native atrioventricular valve.

In some applications of the present invention, the one or more valve support anchors are configured to be anchored to the one or more commissures from ventricular surfaces thereof.

In some applications of the present invention, the one or more valve support guide members includes one valve support guide member that is looped through first and second commissures of the atrioventricular valve in a manner in which a looped portion of the valve support guide member is disposed in a ventricle of the patient and first and second free ends of the valve support guide member are accessible from a site outside a body of the patient.

In some applications of the present invention, the one or more valve support anchors includes first and second tissue anchors, the first and second tissue anchors being configured to be anchored to respective first and second commissures of the atrioventricular valve of the patient.

In some applications of the present invention:

the one or more valve support anchors each include one or more radially-expandable prongs, and the one or more prongs are disposed within a sheath in a compressed state prior to the anchoring, and exposed from within the sheath in order to expand and facilitate anchoring of the valve support anchor to the respective commissures.

In some applications of the present invention, the prosthetic valve includes two or more prosthetic leaflets.

In some applications of the present invention, the native atrioventricular valve includes a mitral valve, and the prosthetic valve includes three prosthetic leaflets.

In some applications of the present invention, the valve support guide members are removable from the patient following the anchoring of the prosthetic valve support at the atrioventricular valve.

In some applications of the present invention, the valve support is shaped so as to define a distal portion which is configured to push aside, at least in part, native leaflets of the valve of the patient.

In some applications of the present invention, the one or more valve support anchors are advanceable along the one or more valve support guide members.

In some applications of the present invention, the valve support is shaped so as to define one or more holes, the one or more holes being configured to facilitate slidable passage therethrough of a respective one of the one or more valve support Guide members.

In some applications of the present invention, the prosthetic valve is shaped so as to define one or more snares configured to ensnare one or more native leaflets of the native valve of the patient.

In some applications of the present invention, the one or more valve support anchors includes one or more ventricular anchors, and the apparatus further includes one or more atrial anchors, each atrial anchor being configured to be advanced toward an atrial surface of the valve support and anchor in place the valve support in a vicinity of a respective one of the ventricular anchors.

In some applications of the present invention, the apparatus includes one or more delivery lumens, and:

each one of the one or more valve support anchors is removably coupled to a distal end of a respective delivery lumen, the delivery lumen is configured to facilitate advancement of the one or more anchors along the one or more guide members, and the delivery lumen is decoupled from the anchor following the anchoring of the anchor to the one or more commissures.

In some applications of the present invention, the one or more valve support guide members are removable from the body of the patient following the advancement of the one or more anchors along the one or more guide members.

In some applications of the present invention:

the valve support is shaped so as to define one or more holes, the one or more holes are configured to facilitate slidable passage therethrough of a respective one of the one or more delivery lumens, and the one or more delivery lumens are decoupleable from the respective valve support anchor following the anchoring of the valve support to at least the one or more commissures.

In some applications of the present invention, the one or more delivery lumens are removable from the body of the patient following the anchoring of the valve support to at least the one or more commissures.

In some applications of the present invention, the valve support includes an annular element and a generally cylindrical element coupled to the annular element, the generally cylindrical element being configured to push aside native leaflets of the native valve, the cylindrical element has first and second ends and a cylindrical body that is disposed between the first and second ends.

In some applications of the present invention, the apparatus includes one or more annular element tissue anchors, the annular element has an upper surface and a lower surface, and the lower surface is coupled to the one or more annular element tissue anchors, the one or more annular element tissue anchors being configured to puncture tissue of a native annulus of the native valve of the patient.

In some applications of the present invention, one or more annular element tissue anchors includes a plurality of annular element tissue anchors positioned around the lower surface of the annular element.

In some applications of the present invention, the one or more annular element tissue anchors includes a first commissural anchor configured to puncture tissue of the native valve at a first commissure thereof, and a second commissural anchor configured to puncture tissue of the native valve at a second commissure thereof.

In some applications of the present invention, each anchor of the one or more annular element tissue anchors includes a distal pointed tip and one or more radially-expandable prongs, the prongs being configured to expand and facilitate anchoring of the anchor and restrict proximal motion of the annular element tissue anchor.

In some applications of the present invention, the apparatus includes one or more prosthetic valve guide members reversibly couplable to the cylindrical element in a vicinity of the second end of the cylindrical element, the prosthetic valve guide members being configured to facilitate advancement of the prosthetic valve therealong and toward the valve support.

In some applications of the present invention:

the first end of the cylindrical element is coupled to the annular element, during a first period, the second end of the cylindrical element is disposed above the annular element in a manner in which the body of the cylindrical element is disposed above the annular element, and the cylindrical element is invertible in a manner in which, during a second period, the second end of the cylindrical element is disposed below the annular element and the body of the cylindrical element is disposed below the annular element.

In some applications of the present invention:

during the first period, the second end of the cylindrical element is disposed in an atrium of a heart of the patient and the annular element is positioned along an annulus of the native valve, the prosthetic valve is advanceable along the one or more prosthetic valve guide members into a ventricle of the heart of the patient, and in response to advancement of the prosthetic valve into the ventricle, the one or more prosthetic valve guide members are pulled into the ventricle and pull the second end and the body of the cylindrical element into the ventricle to invert the cylindrical element.

There is further provided, in accordance with some applications of the present invention, a method, including:

advancing one or more valve support guide members toward one or more commissures of a native atrioventricular valve of a patient;

advancing along the one or more valve support guide members one or more valve support tissue anchors toward the one or more commissures;

anchoring the one or more valve support tissue anchors to the one or more commissures;

anchoring a prosthetic valve support at the native atrioventricular valve by anchoring the prosthetic valve support at least the one or more commissures; and coupling a prosthetic valve to the prosthetic valve support.

In some applications of the present invention, the method includes removing the one or more valve support guide members following the anchoring of the prosthetic valve support at the native atrioventricular valve.

In some applications of the present invention, advancing the one or more valve support guide members toward the one or more commissures includes advancing one guide member and looping the one guide member through first and second commissures of the native atrioventricular valve in a manner in which a looped portion of the guide member is disposed in a ventricle of the patient and first and second free ends of the guide member are accessible from a site outside a body of the patient.

In some applications of the present invention, anchoring the one or more valve support anchors includes anchoring the one or more valve support anchors to ventricular surface of the respective commissures of the native valve.

In sonic applications of the present invention, anchoring the one or more valve support anchors includes anchoring first and second tissue anchors to respective first and second commissures of the native valve.

In some applications of the present invention:
advancing along the one or more valve support guide members the one or more valve support tissue anchors includes advancing the one or more valve support tissue anchors within a sheath, and
anchoring the one or more valve support tissue anchors includes exposing the one or more valve support anchors from within the sheath and facilitating radial expansion of one or more radially-expandable prongs of the one or more anchors.

In some applications of the present invention, coupling the prosthetic valve to the prosthetic valve support includes coupling a prosthetic valve having two or more leaflets.

In some applications of the present invention, the native atrioventricular valve includes a mitral valve of the patient, and coupling the prosthetic valve to the prosthetic valve support includes coupling a prosthetic valve having three leaflets.

In some applications of the present invention, anchoring the prosthetic valve support includes pushing aside, at least in part, native leaflets of the valve of the patient by at least a portion of the support.

In some applications of the present invention, the prosthetic valve support is coupled to one or more annulus tissue anchors, and anchoring the prosthetic valve support includes pushing the one or more annulus tissue anchors into tissue of an annulus of the native valve.

In some applications of the present invention, coupling the prosthetic valve to the prosthetic valve support includes ensnaring one or more native leaflets of the native valve of the patient by a portion of the prosthetic valve.

In sonic applications of the present invention, the one or more valve support anchors includes one or more ventricular anchors, and the method further includes advancing one or more atrial anchors to an atrial surface of the valve support, and anchoring in place the valve support in a vicinity of a respective one of the ventricular anchors.

In some applications of the present invention, the method includes advancing the valve support along the one or more valve support guide members prior to the anchoring of the valve support.

In some applications of the present invention, the valve support is shaped so as to define one or more holes, and advancing the valve support along the one or more valve support guide members includes threading the one or more valve support guide members through the one or more holes of the valve support and sliding the valve support along the one or more guide members.

In some applications of the present invention, the method includes removing the one or more valve support guide members from a body of the patient following the anchoring of the valve support.

In some applications of the present invention,
the valve support includes:
an annular element, and
a generally cylindrical element having first and second ends and a cylindrical body that is disposed between the first and second ends, the first end being coupled to the annular element; and anchoring of the valve support, including anchoring the valve support in a manner in which:
the annular element is positioned along an annulus of the native valve,
the second end of the cylindrical element is disposed above the annular element in an atrium of a heart of the patient, and
the body of the cylindrical element is disposed above the annular element.

In some applications of the present invention, the method includes, following the anchoring, inverting the cylindrical element to pull the second end of the cylindrical element below the annular element and into a ventricle of the heart, in a manner in which the body of the cylindrical element is disposed below the annular element and pushes aside one or more native leaflets of the valve of the patient.

In some applications of the present invention:
inverting the cylindrical element includes advancing the prosthetic valve along one or more prosthetic valve guide members reversibly coupled to the cylindrical element in a vicinity of the second end thereof,
advancing the prosthetic valve includes advancing the prosthetic valve into the ventricle to pull the prosthetic valve guide members and the second end of the cylindrical element into the ventricle, and
the method further includes following the advancing of the prosthetic valve into the ventricle, pulling proximally the prosthetic valve such that a proximal portion of the valve contacts the valve support.

In some applications of the present invention, pulling the prosthetic valve proximally includes ensnaring the one or more leaflets of the valve by a portion of the prosthetic valve.

In some applications of the present invention, advancing the one or more valve support anchors includes:
providing a respective delivery lumen coupled at a distal end thereof to each one of the one or more anchors,
advancing each delivery lumen along a respective one of the one or more valve support guide members,
facilitating anchoring of each one of the one or more anchors to the one or more commissures by the respective delivery lumen, and
decoupling the delivery lumen from each one of the one or more valve support anchors following the anchoring of the one or more valve support anchors.

In some applications of the present invention, the method includes removing the one or more valve support guide members from a body of the patient following the anchoring of each one of the one or more valve support anchors to the one or more commissures.

In some applications of the present invention, the method includes advancing the prosthetic valve support along the one or more delivery lumens prior to the anchoring the support at the native atrioventricular valve.

In some applications of the present invention, the valve support is shaped so as to define one or more holes, and advancing the valve support along the one or more delivery lumens includes threading the one or more delivery lumens through the one or more holes of the valve support and sliding the valve support along the one or more delivery lumens.

In some applications of the present invention, the method includes removing the one or more delivery lumens from a body of the patient following the anchoring the support at the atrioventricular valve.

There is additionally provided, in accordance with some applications of the present invention, apparatus including a valve support for receiving a prosthetic valve, the valve support including:

an annular element configured to be positioned along a native annulus of a native atrioventricular valve of a patient; and a flexible generally cylindrical element configured to be positioned in the native atrioventricular valve of the patient and to push aside native leaflets of the native valve, the cylindrical element having first and second ends and a cylindrical body that is disposed between the first and second ends, and:
  the first end of the cylindrical element is coupled to the annular element,
  during a first period, the second end of the cylindrical element is disposed above the annular element in a manner in which the body of the cylindrical element is disposed above the annular element, and
  the cylindrical element is invertible in a manner in which, during a second period, the second end of the cylindrical element is disposed below the annular element and the body of the cylindrical element is disposed below the annular element.

In some applications of the present invention, the cylindrical element includes a flexible wireframe covered by a fabric.

In some applications of the present invention, the valve support is collapsible for transcatheter delivery and expandable to contact the native atrioventricular valve.

In some applications of the present invention, the annular element has an upper surface and a lower surface, the lower surface is coupled to one or more annular element tissue anchors configured to puncture tissue of the native annulus of the patient.

In some applications of the present invention, the one or more annular element tissue anchors includes a plurality of annular element tissue anchors positioned around the lower surface of the annular element.

In some applications of the present invention, the one or more annular element tissue anchors includes a first commissural annular element tissue anchor configured to puncture tissue of the native valve at a first commissure thereof, and a second commissural annular element tissue anchor configured to puncture tissue of the native valve at a second commissure thereof.

In some applications of the present invention, each anchor of the one or more annular element tissue anchors includes a distal pointed tip and one or more radially-expandable prongs, the prongs being configured to expand and facilitate anchoring of the anchor and restrict proximal motion of the annular element tissue anchor.

In some applications of the present invention, the apparatus includes one or more valve support guide members configured to be delivered to one or more commissures of the native atrioventricular valve of the patient, the one or more valve support guide members are configured to facilitate advancement of the valve support toward the native valve.

In some applications of the present invention, the valve support is shaped so as to define one or more holes, the one or more holes configured to facilitate slidable passage therethrough of a respective one of the one or more valve support guide members.

In some applications of the present invention, the one or more valve support guide members includes one valve support guide member that is looped through first and second commissures of the atrioventricular valve in a manner in which a looped portion of the valve support guide member is disposed in a ventricle of the patient and first and second free ends of the valve support guide member are accessible from a site outside a body of the patient.

In some applications of the present invention, the apparatus includes one or more valve support tissue anchors configured to be advanceable along the one or more valve support guide members and anchored to the one or more commissures of the valve.

In some applications of the present invention, the one or more valve support anchors includes one or more ventricular anchors, and the apparatus further includes one or more atrial anchors, each atrial anchor being configured to be advanced toward an atrial surface of the valve support and anchor in place the valve support in a vicinity of a respective one of the ventricular anchors.

In some applications of the present invention, the valve support guide members are removable from the patient following the anchoring of the valve support at the atrioventricular valve.

In some applications of the present invention, the one or more valve support anchors are configured to be anchored to the one or more commissures from ventricular surfaces thereof prior to advancement of the valve support.

In some applications of the present invention, the one or more valve support tissue anchors includes first and second valve support tissue anchors, the first and second valve support tissue anchors being configured to be anchored to respective first and second commissures of the atrioventricular valve of the patient.

In some applications of the present invention:
  the one or more valve support tissue anchors each include one or more radially-expandable prongs, and
  the one or more prongs are disposed within a sheath in a compressed state prior to the anchoring and exposed from within the sheath in order to expand and facilitate anchoring of the anchor to the respective commissures.

In some applications of the present invention, the apparatus includes one or more prosthetic valve guide members reversibly couplable to the cylindrical element in a vicinity of the second end of the cylindrical element, the prosthetic valve guide members being configured to facilitate advancement of the prosthetic valve therealong and toward the valve support.

In some applications of the present invention, the apparatus includes the prosthetic valve, the prosthetic valve is couplable to the valve support.

In some applications of the present invention:
  during the first period, the second end of the cylindrical element is disposed in an atrium of a heart of the patient and the annular element is positioned along an annulus of the native valve,
  the prosthetic valve is advanceable along the one or more prosthetic valve guide members into a ventricle of the heart of the patient, and
  in response to advancement of the prosthetic valve into the ventricle, the one or more prosthetic valve guide members are pulled into the ventricle and pull the second end of the cylindrical element into the ventricle to invert the cylindrical element.

In some applications of the present invention, the prosthetic valve is collapsible for transcatheter delivery and expandable when exposed from within a delivery catheter.

In some applications of the present invention, the prosthetic valve includes two or more prosthetic leaflets.

In some applications of the present invention, the native atrioventricular valve includes a mitral valve, and the prosthetic valve includes three prosthetic leaflets.

In some applications of the present invention, the prosthetic valve guide members are removable from the patient following the anchoring of the prosthetic valve at the atrioventricular valve.

In some applications of the present invention, the prosthetic valve is shaped so as to define one or more snares configured to ensnare one or more native leaflets of the native valve of the patient.

There is yet additionally provided, in accordance with some applications of the present invention, a method, including:

advancing toward a native atrioventricular valve of a heart of a patient, a valve support including:

an annular element, and a generally cylindrical element having first and second ends and a cylindrical body that is disposed between the first and second ends, the first end being coupled to the annular element;

anchoring the annular element to an annulus of the native atrioventricular valve, following the anchoring, the second end of the cylindrical element is disposed above the annular element in an atrium of the heart, in a manner in which the body of the cylindrical element is disposed above the annular element; and following the anchoring, inverting the cylindrical element to pull the second end of the cylindrical element below the annular element and into a ventricle of the heart, in a manner in which the body of the cylindrical element is disposed below the annular element and pushes aside one or more native leaflets of the valve of the patient.

In some applications of the present invention, anchoring the annular element to the annulus of the native atrioventricular valve includes:

advancing one or more valve support anchors that are distinct from the valve support toward one or more commissures of the heart, and anchoring the annular element to the annulus using the one or more positioning anchors.

In some applications of the present invention, the annular element is coupled to one or more annular element tissue anchors, and anchoring the annular element includes pushing the one or more annular element tissue anchors into tissue of the annulus.

In some applications of the present invention:

inverting the cylindrical element includes advancing a prosthetic valve along one or more valve guide members reversibly coupled to the cylindrical element in a vicinity of the second end thereof, advancing the prosthetic valve includes advancing the prosthetic valve into the ventricle to pull the guide members and the second end of the cylindrical element into the ventricle, and the method further includes following the advancing of the prosthetic valve into the ventricle, pulling proximally the prosthetic valve such that a proximal portion of the valve contacts the valve support.

In some applications of the present invention, pulling the prosthetic valve proximally includes ensnaring the one or more leaflets of the valve by a portion of the prosthetic valve.

There is also provided, in accordance with some applications of the present invention, apparatus including a valve support for receiving a prosthetic valve, the valve support including:

an annular element configured to be positioned along a native annulus of a native atrioventricular valve of a patient, the annular element having upper and lower surfaces; and one or more annular element tissue anchors coupled to the lower surface of the annular element, the one or more annular element tissue anchors being configured to puncture tissue of the native annulus of the patient.

In some applications of the present invention, the valve support is collapsible for transcatheter delivery and expandable to contact the native atrioventricular valve.

In some applications of the present invention, the one or more annular element tissue anchors includes a plurality of annular element tissue anchors positioned around the lower surface of the annular element.

In some applications of the present invention, the one or more annular element tissue anchors includes a first commissural annular element tissue anchor configured to puncture tissue of the native valve at a first commissure thereof, and a second commissural annular element tissue anchor configured to puncture tissue of the native valve at a second commissure thereof.

In some applications of the present invention, each anchor of the one or more annular element tissue anchors includes a distal pointed tip and one or more radially-expandable prongs, the prongs being configured to expand and facilitate anchoring of the anchor and restrict proximal motion of the anchor.

In some applications of the present invention, the apparatus includes one or more valve support guide members configured to be delivered to one or more commissures of the native atrioventricular valve of the patient, the one or more valve support guide members are configured to facilitate advancement of the valve support toward the native valve.

In some applications of the present invention, the valve support is shaped so as to define one or more holes, the one or more holes configured to facilitate slidable passage therethrough of a respective one of the one or more valve support guide members.

In some applications of the present invention, the one or more valve support guide members includes one valve support guide member that is looped through first and second commissures of the atrioventricular valve in a manner in which a looped portion of the valve support guide member is disposed in a ventricle of the patient and first and second free ends of the valve support guide member are accessible from a site outside a body of the patient.

In some applications of the present invention, the apparatus includes one or more valve support tissue anchors that are distinct from the valve support and are configured to be advanceable along the one or more valve support guide members and anchored to the one or more commissures of the valve.

In some applications of the present invention, the one or more valve support anchors includes one or more ventricular anchors, and the apparatus further includes one or more atrial anchors, each atrial anchor being configured to be advanced toward an atrial surface of the valve support and anchor in place the valve support in a vicinity of a respective one of the ventricular anchors.

In some applications of the present invention, the one or more valve support guide members are removable from the patient following the anchoring of the valve support at the atrioventricular valve.

In some applications of the present invention, the one or more valve support tissue anchors are configured to be anchored to the one or more commissures from ventricular surfaces thereof prior to advancement of the valve support.

In some applications of the present invention, the one or more valve support tissue anchors includes first and second valve support tissue anchors, the first and second valve support tissue anchors being configured to be anchored to respective first and second commissures of the atrioventricular valve of the patient.

In some applications of the present invention:
the one or more valve support tissue anchors each include one or more radially-expandable prongs, and
the one or more prongs are disposed within a sheath in a compressed state prior to the anchoring and exposed from within the sheath in order to expand and facilitate anchoring of the anchor to the respective commissures.

In some applications of the present invention, the valve support further includes a flexible generally cylindrical element coupled to the annular element and configured to be positioned in the native atrioventricular valve of the patient and to push aside native leaflets of the native valve, the cylindrical element having first and second ends and a cylindrical body that is disposed between the first and second ends.

In some applications of the present invention, the cylindrical element includes a flexible wireframe covered by a fabric.

In some applications of the present invention, the apparatus includes one or more prosthetic valve guide members reversibly couplable to the cylindrical element in a vicinity of the second end of the cylindrical element, the prosthetic valve guide members being configured to facilitate advancement of the prosthetic valve therealong and toward the valve support.

In some applications of the present invention, the apparatus includes the prosthetic valve, the prosthetic valve is couplable to the valve support.

In some applications of the present invention:
the first end of the cylindrical element is coupled to the annular element,
during a first period, the second end of the cylindrical element is disposed above the annular element in a manner in which the body of the cylindrical element is disposed above the annular element, and
the cylindrical element is invertible in a manner in which, during a second period, the second end of the cylindrical element is disposed below the annular element and the body of the cylindrical element is disposed below the annular element.

In some applications of the present invention:
during the first period, the second end of the cylindrical element is disposed in an atrium of a heart of the patient,
the prosthetic valve is advanceable along the one or more prosthetic valve guide members into a ventricle of the heart of the patient, and
in response to advancement of the prosthetic valve into the ventricle, the one or more prosthetic valve guide members are pulled into the ventricle and pull the second end of the cylindrical element into the ventricle to invert the cylindrical element.

The present invention will be more fully understood from the following detailed description of embodiments thereof, taken together with the drawings, in which:

BRIEF DESCRIPTION OF THE DRAWINGS

FIGS. 2G-K are schematic illustrations of the advancement of a prosthetic valve and the coupling of the prosthetic valve to the valve support, in accordance with some applications of the present invention;

FIGS. 3A-C are schematic illustrations of a valve support that has a cylindrical element that is invertible, in accordance with some applications of the present invention;

FIGS. 5A-D are schematic illustrations of the valve support of FIGS. 4A-B being implanted in the native valve of the patient and facilitating implantation of a prosthetic valve, in accordance with some applications of the present invention.

DETAILED DESCRIPTION OF THE EMBODIMENTS

Figure 1A:
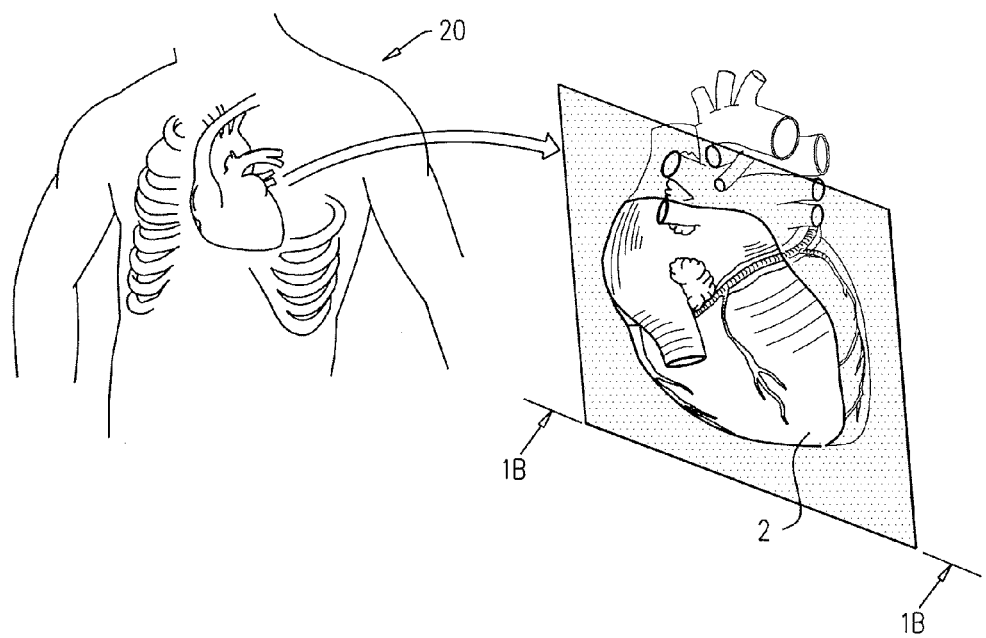
FIGS. 1A-B are schematic illustrations of advancement of one or more guide members toward respective commissures of a mitral valve, in accordance with some applications of the present invention.
Figure 1B:
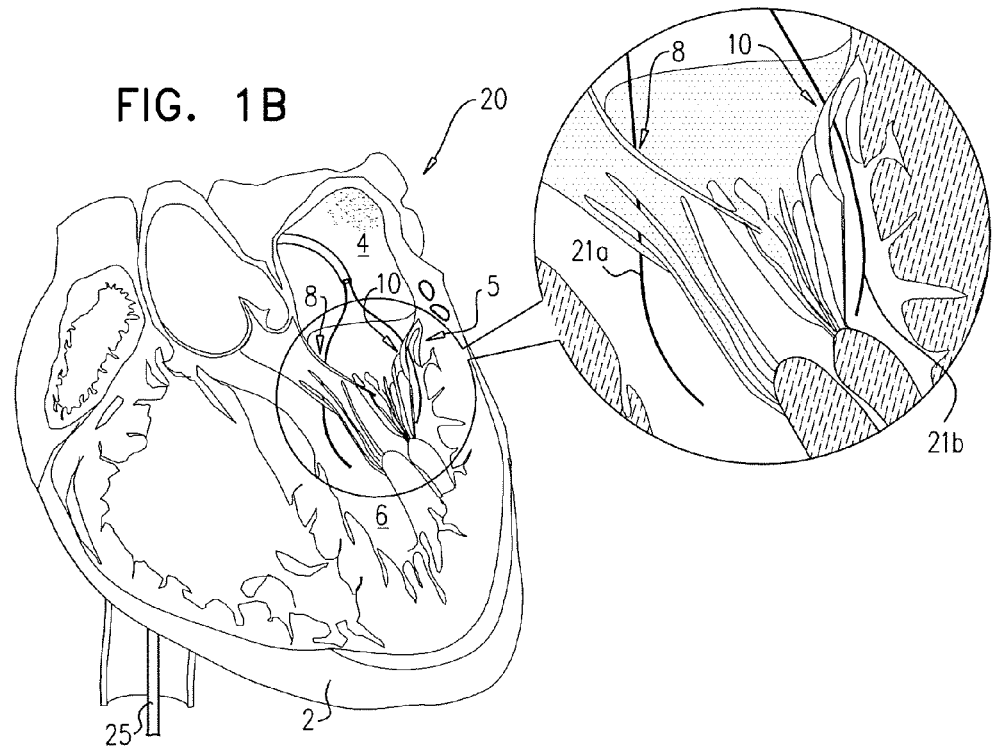
Figure 1C:
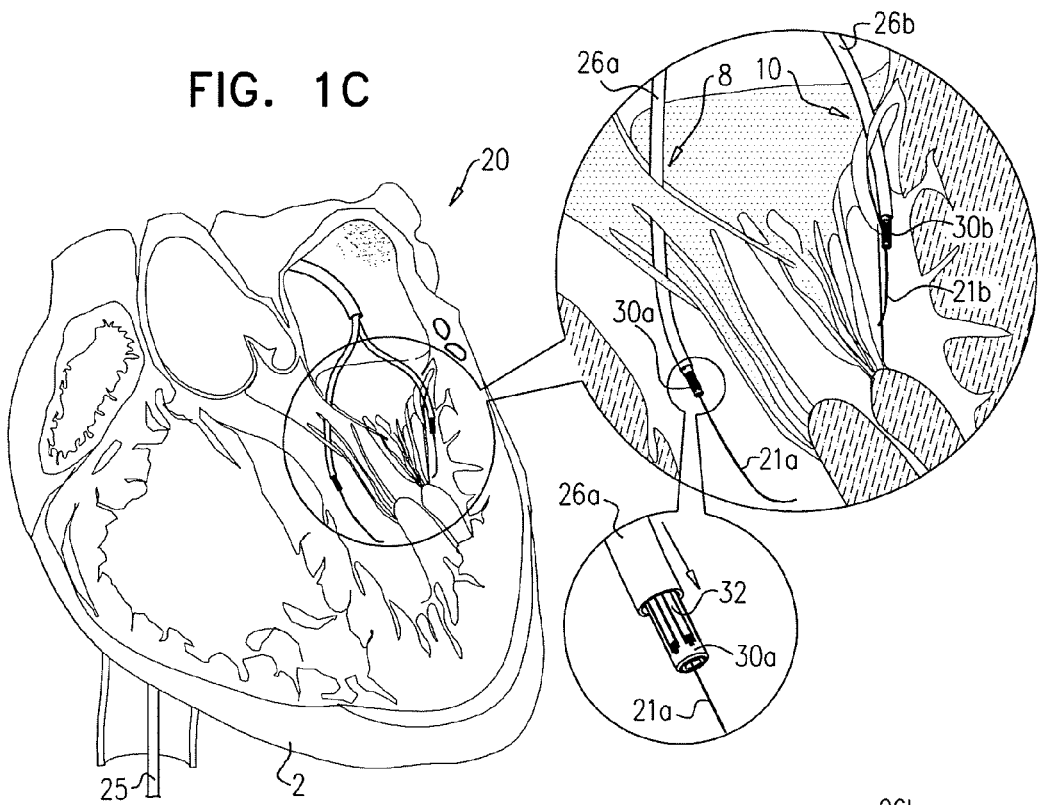
FIGS. 1C-D are schematic illustrations of the advancement and deployment of commissural anchors via the guide members, in accordance with some applications of the present invention.
Figure 6:
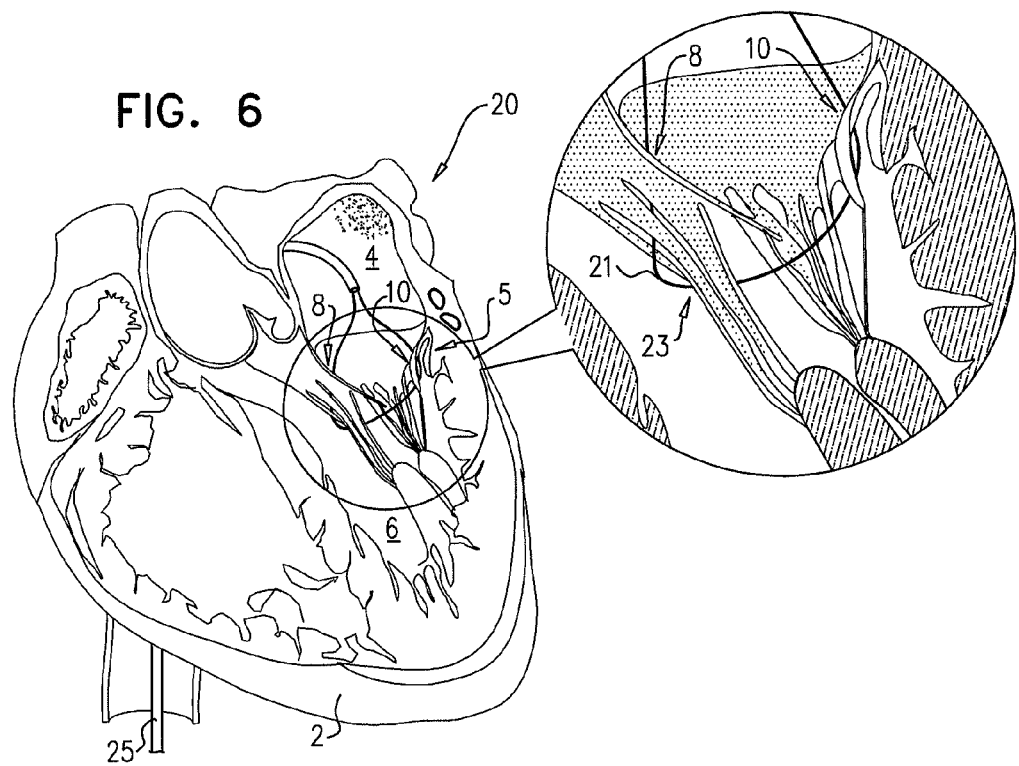
FIG. 6 is a schematic illustration of advancement of a guide member having a looped portion, toward commissures of a mitral valve, in accordance with some applications of the present invention.

Reference is now made to FIGS. 1A-B, which are schematic illustrations of a system 20 for replacing an atrioventricular valve 5 of a patient comprising one or more guide members 21 (e.g., guide member 21a and guide member 21b) which are advanced toward first and second commissures 8 and 10 of valve 5 of a heart 2 of the patient, in accordance with some applications of the present invention. For some applications, and as shown in FIG. 1B, guide members 21a and 21b comprise distinct guide members. Alternatively, as shown in FIG. 6, only one guide member 21 is looped through commissures 8 and 10 in a manner in which the guide member defines a looped portion 23 between commissures 8 and 10 (i.e., a portion of the guide member that is disposed in a ventricle 6 of heart 2), and first and second free ends which are disposed and accessible at a site outside the body of the patient. For such applications, the guide member defines portions 21a and 21b.

For some applications, guide members 21 (e.g., guide members 21a and 21b) comprise guide wires having a diameter of 0.035 inches.

The transcatheter procedure typically begins with the advancing of a semi-rigid guide wire into a right atrium 4 of the patient. The semi-rigid guide wire provides a guide for the subsequent advancement of a sheath 25 therealong and into the right atrium. Once sheath 25 has entered the right atrium, the semi-rigid guide wire is retracted from the patient's body. Sheath 25 typically comprises a 13-20 F sheath, although the size may be selected as appropriate for a given patient. Sheath 25 is advanced through vasculature into the right atrium using a suitable point of origin typically determined for a given patient. For example:

sheath 25 may be introduced into the femoral vein of the patient, through an inferior vena cava, into the right atrium, and into the left atrium transseptally, typically through the fossa ovalis;

sheath 25 may be introduced into the basilic vein, through the subclavian vein to the superior vena cava, into the right atrium, and into the left atrium transseptally, typically through the fossa ovalis; or sheath 25 may be introduced into the external jugular vein, through the subclavian vein to the superior vena cava, into the right atrium, and into the left atrium transseptally, typically through the fossa ovalis.

In some applications of the present invention, sheath 25 is advanced through the inferior vena cava of the patient and into the right atrium using a suitable point of origin typically determined for a given patient.

Sheath 25 is advanced distally until sheath 25 reaches the interatrial septum. For some applications, a resilient needle and a dilator (not shown) are advanced through the sheath and into the heart. In order to advance the sheath transseptally into the left atrium, the dilator is advanced to the septum, and the needle is pushed from within the dilator and is allowed to puncture the septum to create an opening that facilitates passage of the dilator and subsequently the sheath therethrough and into the left atrium. The dilator is passed through the hole in the septum created by the needle. Typically, the dilator is shaped to define a hollow shaft for passage along the needle, and the hollow shaft is shaped to define a tapered distal end. This tapered distal end is first advanced through the hole created by the needle. The hole is enlarged when the gradually increasing diameter of the distal end of the dilator is pushed through the hole in the septum.

The advancement of sheath 25 through the septum and into the left atrium is followed by the extraction of the dilator and the needle from within sheath 25.

FIGS. 1C-D and 2A-B show advancement of one or more tissue anchors 30a and 30b along guide members 21a and 21b, respectively. Anchors 30a and 30b comprise a flexible, biocompatible material (e.g., nitinol) and comprise one or more (e.g., a plurality of) radially-expandable prongs 32 (e.g., barbs). Each anchor 30a and 30b is reversibly coupled to a respective delivery lumen 27a and 27b. Each delivery lumen 27 slides around a respective guide member 21. A respective surrounding sheath 26a and 26b surrounds each delivery lumen 27a and 27b and around anchors 30a and 30b at least in part in order to compress and prevent expansion of prongs 32 of tissue anchors 30a and 30b.

Figure 1D:
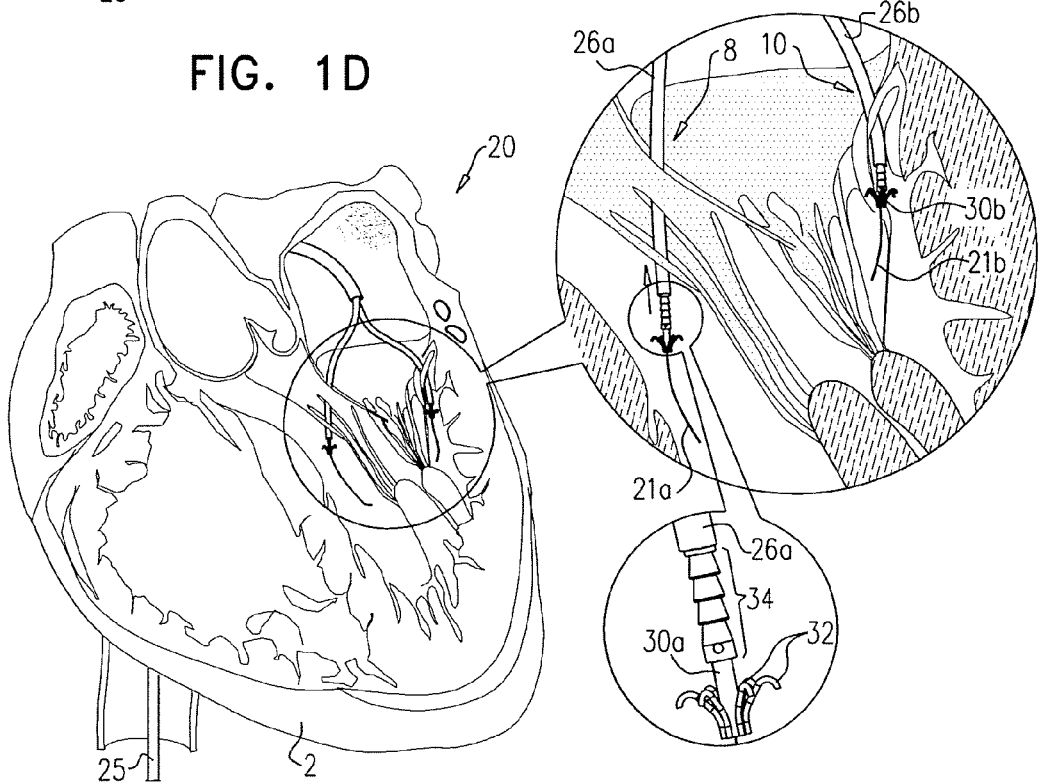

As shown in FIG. 1D, the distal ends of lumens 27a and 27b are reversibly coupled to ribbed crimping structures 34. As described hereinbelow, anchors 30a and 30b are anchored to ventricular surfaces of commissures 8 and 10. Following the anchoring, ribbed crimping structures 34 extend from anchors 30a and 30b through commissures 8 and 10, respectively, and toward the atrial surfaces of commissures 8 and 10. Ribbed crimping structures 34 are configured to facilitate anchoring of a valve support (described hereinbelow) to the atrial surfaces of commissures 8 and 10.

Anchors 30a and 30b, ribbed crimping structures 34, and the distal ends of surrounding sheaths 26a and 26b are advanced into ventricle 6. Subsequently, anchors 30a and 30b are pushed distally from within sheaths 26a and 26b, (or sheaths 26a and 26b are pulled proximally with respect to anchors 30a and 30b) to expose anchors 30a and 30b. As anchors 30a and 30b are exposed from within sheaths 26a and 26b, prongs 32 are free to expand, as shown in FIG. 1D. Prongs 32 expand such that anchors 30a and 30b assume a flower shape. Prongs 32, collectively in their expanded state, create a larger surface area to engage tissue than in their compressed states. Following the exposing of anchors 30a and 30b, sheaths 26a and 26b are extracted.

Figure 2A:
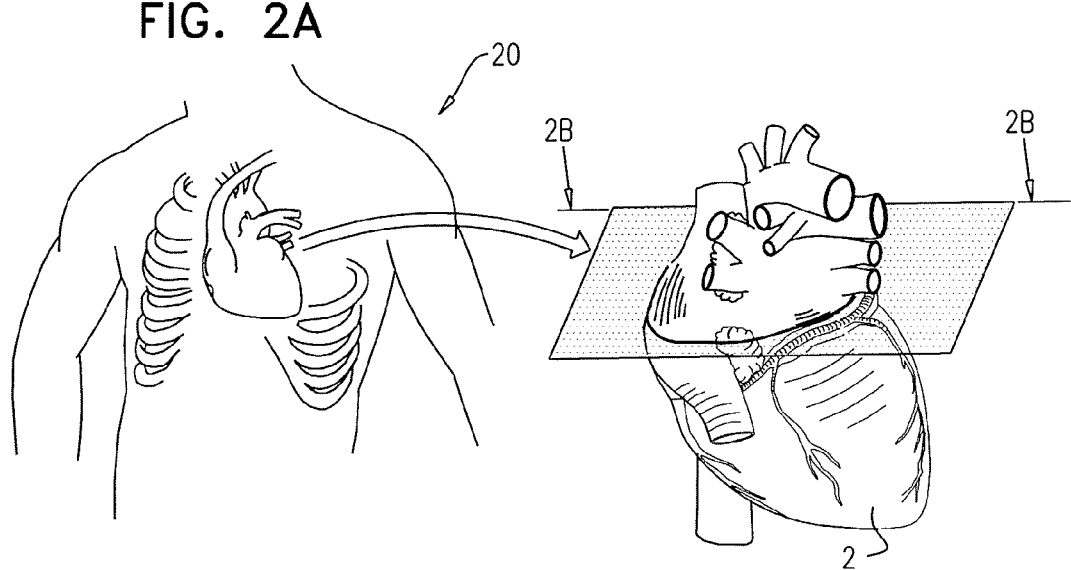
FIGS. 2A-D are schematic illustrations of the advancement of a prosthetic valve support toward a native atrioventricular valve of a patient, in accordance with some applications of the present invention.
Figure 2B:
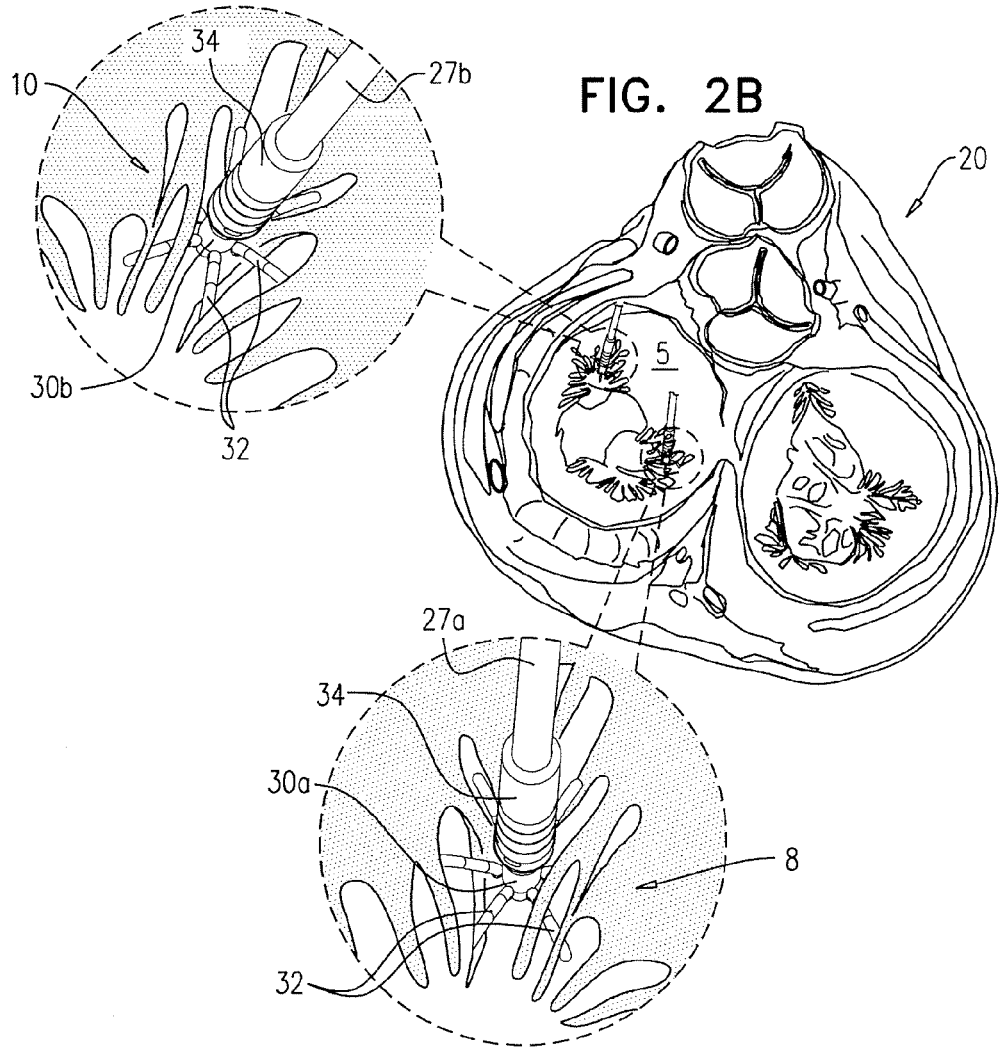

As shown in FIG. 2B, lumens 27a and 27b are pulled proximally so that prongs 32 of anchors 30a and 30b engage respective ventricular surface of commissures 8 and 10. Prongs 32 create a large surface area which restricts proximal motion of anchors 30a and 30b from commissures 8 and 10, respectively.

For some applications, following the anchoring of anchors 30a and 30b to commissures 8 and 10, respectively, guide members 21a and 21b are removed from the body of the patient.

Figure 2C:
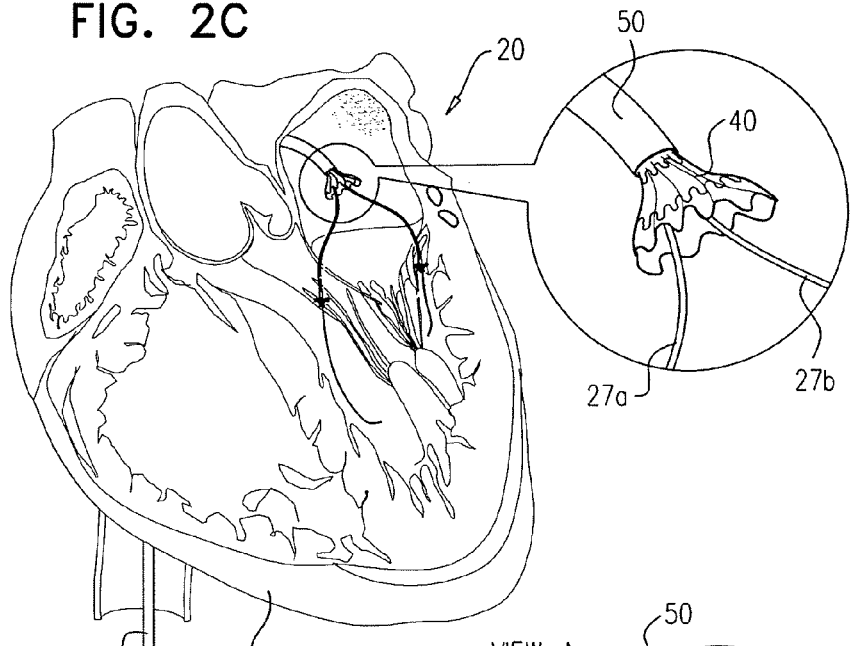
Figure 2D:
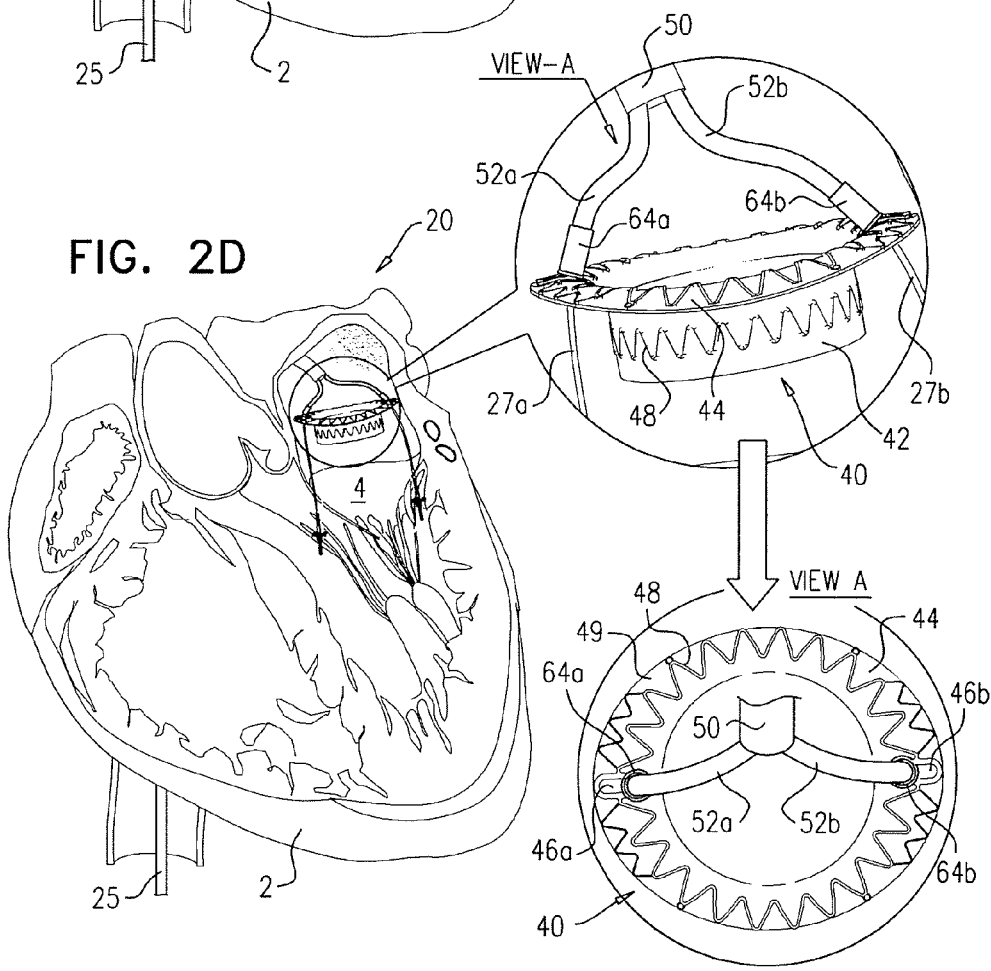

Reference is now made to FIGS. 2C-F, which are schematic illustrations of the advancement of a prosthetic valve support 40 along lumens 27a and 27b, in accordance with some applications of the present invention. In such a manner, lumens 27a and 27b function as valve support guide members. Support 40 comprises a collapsible skirt having a proximal annular element 44 and a distal cylindrical element 42. Support 40 is configured to assume a collapsed state (e.g., surrounded by a sheath or overtube 50 shown in FIG. 2C) for minimally-invasive delivery to the diseased native valve, such as by percutaneous or transluminal delivery using one or more catheters. FIG. 2C and the other figures show support 40 in an expanded state after delivery in right atrium 4 and advancement toward the native valve. As shown in FIG. 2D, support 40 is shaped so as to define one or more (e.g., two, as shown in View A) holes 46a and 46b for slidable advancement of support 40 along lumens 27a and 27b, respectively. That is, prior to introduction of support 40 into the body of the patient, lumens 27a and 27b are threaded through holes 46a and 46b, respectively, and support 40 is slid along lumens 27a and 27b. Support 40 is slid by pushing elements 52a and 52b which surround delivery lumens 27a and 27b, respectively.

It is to be noted that support 40 is slid along lumens 27a and 27b by way of illustration and not limitation. That is, for some applications, following the anchoring of anchors 30a and 30b to commissures 8 and 10, respectively, guide members 21a and 21b are not removed from the body of the patient, but rather lumens 27a and 27b are removed (e.g., by being decoupled from crimping structures 34) leaving behind anchors 30a and 30b and guide members 21a and 21b. Guide members 21a and 21b may then be threaded through holes 46a and 46b, respectively, and support 40 is slid along guide members 21a and 21b. In such a manner, guide members 21a and 21b function as valve support guide members.

Figure 2E:
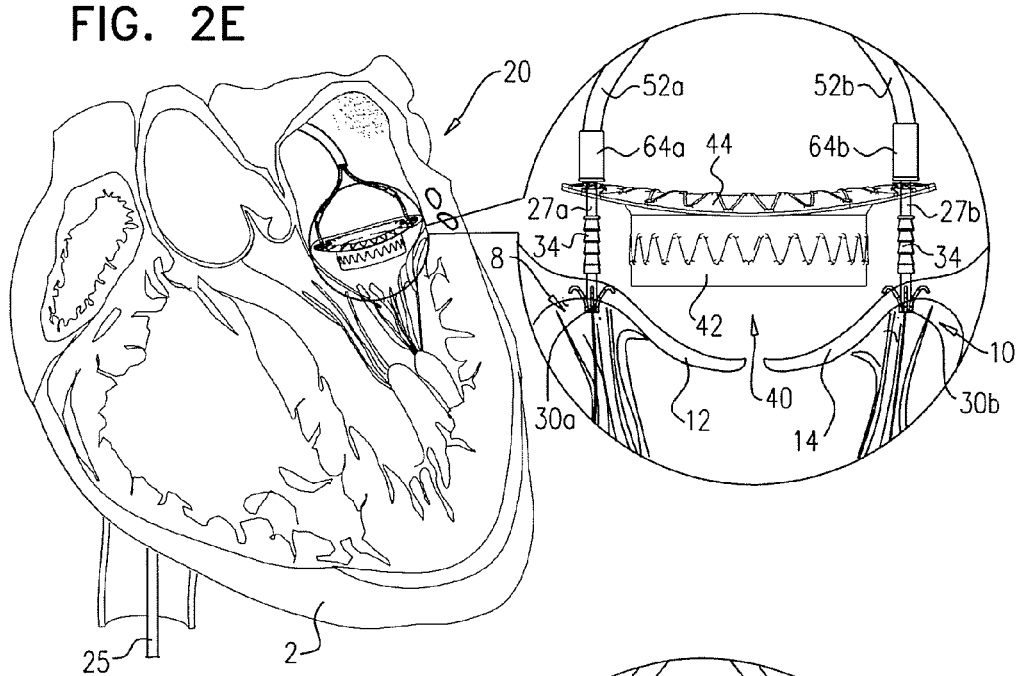
FIGS. 2E-F are schematic illustrations of locking of the prosthetic valve support at the native valve, in accordance with some applications of the present invention.

Support 40 comprises a collapsible flexible support frame 48, which is at least partially covered by a covering 49. Support 40 is configured to be placed at native valve 5, such that cylindrical element 42 passes through the orifice of the native valve and extends towards, and, typically partially into, ventricle 6 (as shown in FIG. 2E). Cylindrical element 42 typically pushes aside and presses against native leaflets of native valve 5 at least in part, which are left in place during and after implantation of the prosthetic valve. Annular element 44 is configured to be placed around a native annulus 11 of the native valve, and to extend at least partially into an atrium 4 such that annular element 44 rests against the native annulus. Annular element 44 is typically too large to pass through the annulus, and may, for example, have an outer diameter of between 30 and 60 mm.

For some applications, collapsible support frame 48 comprises a stent, which comprises a plurality of struts. The struts may comprise, for example, a metal such as nitinol or stainless steel. For some applications frame 48 comprises a flexible metal, e.g., nitinol, which facilitates compression of support 40 within a delivery sheath or overtube 50. For some applications, covering 49 comprises a fabric, such as a woven fabric, e.g., Dacron. Covering 49 is typically configured to cover at least a portion of cylindrical element 42, and at least a portion of annular element 44. The covering may comprise a single piece, or a plurality of pieces sewn together.

As shown in FIG. 2D, pushing elements 52a and 52b are each coupled to locking crimping elements 64a and 64b, respectively. Locking crimping elements 64a and 64b are disposed adjacently, proximally to holes 46a and 46b respectively of valve support 40. These techniques enable the surgeon to readily bring crimping elements 64a and 64b to the appropriate sites along annular element 44, without the need for excessive imaging, such as fluoroscopy.

FIG. 2E shows valve support 40 prior to implantation at annulus 11. As shown, ribbed crimping structures 34 project away from anchors 30a and 30b, through commissures 8 and 10, and toward atrium 4. Valve support 40 is advanced along lumens 27a and 27b toward structures 34 by being pushed by pushing elements 52a and 52b and locking crimping elements 64a and 64b.

Figure 2F:
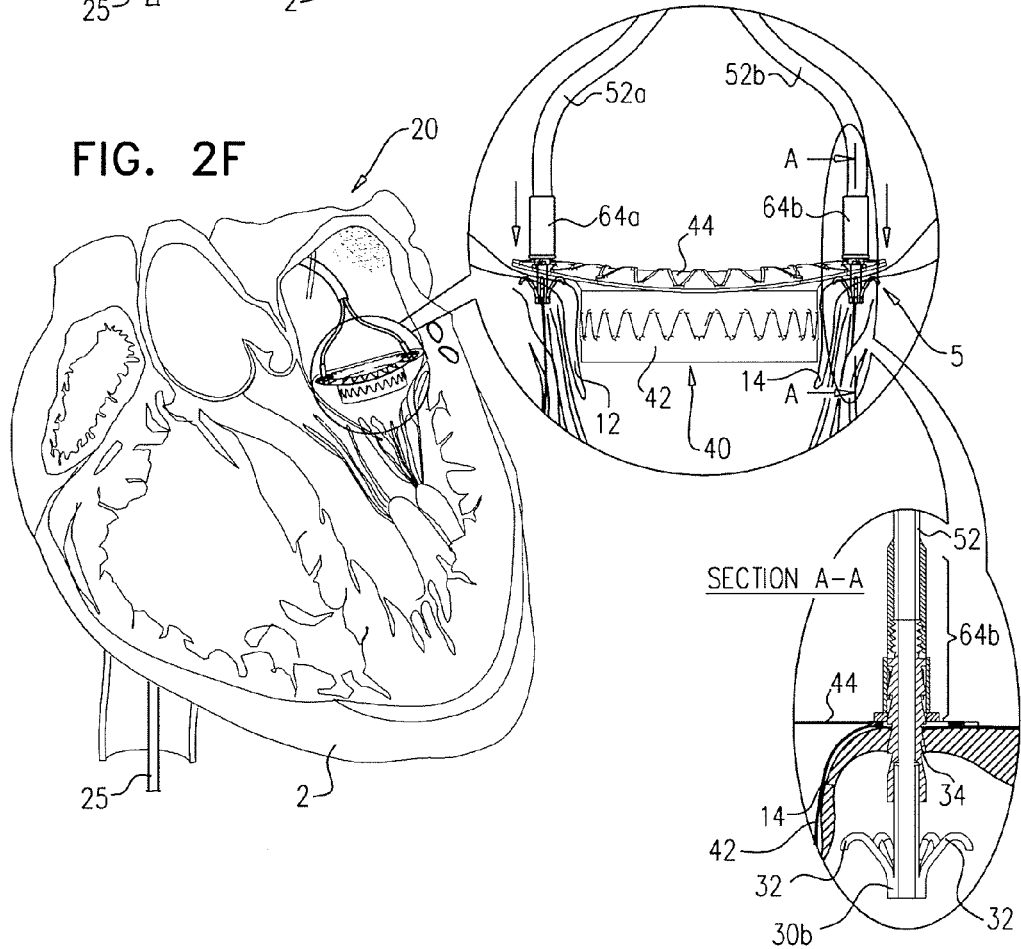

In FIG. 2F, valve support 40 is further pushed by pushing elements 52a and 52b and locking crimping elements 64a and 64b such holes 46a and 46b of support 40 advance around ribbed crimping structures 34. As holes 46a and 46b are advanced around ribbed crimping structures 34, locking crimping elements 64a and 64b advance over and surround ribbed crimping elements 34 to lock in place valve support 40 from an atrial surface of valve 5.

Responsively to the placement of valve support 40 at native valve 5, cylindrical element 42 is positioned partially within ventricle 6 and native leaflets 12 and 14 of native valve 5 are pushed aside.

As shown in section A-A, ribbed crimping structures 34 are shaped so as to define a plurality of male couplings. Locking crimping elements 64a and 64b each comprise a cylindrical element having an inner lumen that is shaped so as to surround a respective ribbed crimping structure 34. Each inner lumen of locking crimping elements 64a and 64b is shaped so as to define female couplings to receive the male couplings of ribbed crimping structure 34. The female couplings of locking crimping element 64 are directioned such that they facilitate distal advancement of locking crimping element 64 while restricting proximal advancement of locking crimping element 64. When the female couplings of locking crimping element 64 receive the male couplings of ribbed crimping structure 34, valve support 40 is locked in place from an atrial surface of valve 5. It is to be noted that for some applications, ribbed crimping elements 34 comprise female couplings, and locking crimping elements 64 comprise male couplings.

Reference is now made to FIGS. 2G-K which are schematic illustrations of the coupling of a prosthetic atrioventricular valve 80 to valve support 40, in accordance with some applications of the present invention. Support 40 receives the prosthetic valve and functions as a docking station. Thus, the docking station is a coupling element that provides coupling between two other elements (in this case, between annulus 11 and the prosthetic valve.)

Following the placement of support 40 at annulus 11, pushing elements 52a and 52b and sheath or overtube 50 are removed from the body of the patient, leaving behind lumens 27a and 27b, as shown in FIG. 2G.

As shown in FIG. 2G, a guide wire 72 is advanced toward ventricle 6 and facilitates the advancement of an overtube 70 through sheath 25 and the positioning of a distal end of overtube 70 within ventricle 6. Overtube 70 facilitates the advancement of prosthetic valve 80 in a compressed state, toward valve support 40.

FIG. 2H shows partial deployment of valve 80 within ventricle 6 of heart 2. Valve 80 is shown comprising a flexible wire frame comprising a plurality of stent struts by way of illustration and not limitation. The wireframe of valve 80 comprises a flexible metal, e.g., nitinol or stainless steel. It is to be noted that the wireframe of valve 80 is covered by a covering (not shown for clarity of illustration) comprising a braided mesh or in a fabric such as a woven fabric, e.g., Dacron. The covering is typically configured to cover at least a portion of the frame. The covering may comprise a single piece, or a plurality of pieces sewn together.

Following the partial deployment of valve 80 in ventricle 6, overtube 70 is pulled proximally to pull valve 80 proximally such that cylindrical element 42 of valve support 40 surrounds a distal portion of prosthetic valve 80. Valve 80 has a tendency to expand such that valve 80 is held in place with respect to valve support 40 responsively to radial forces acted upon valve support 40 by prosthetic valve 80.

Valve 80 comprises a plurality of distal snares 84. When valve 80 is pulled proximally, as described hereinabove, snares 84 ensnare and engage the native leaflets of the atrioventricular valve. By the ensnaring of the native leaflets, snares 84 sandwich the native valve between snares 84 and prosthetic valve support 40. Such ensnaring helps further anchor prosthetic valve 80 to the native atrioventricular valve.

Additionally, as shown in FIG. 2J, valve 80 comprises one or more (e.g., a plurality, as shown) coupling elements 81 at the proximal end of valve 80. Overtube 70, which facilitates the advancement of prosthetic valve 80, is reversibly coupled to valve 80 coupling elements 81.

Prosthetic valve 80 is configured for implantation in and/or at least partial replacement of a native atrioventricular valve 5 of the patient, such as a native mitral valve or a native tricuspid valve. Prosthetic valve 80 is configured to assume a collapsed state for minimally-invasive delivery to the diseased native valve, such as by percutaneous or transluminal delivery using one or more catheters. FIG. 2J shows prosthetic valve 80 in an expanded state after delivery to the native valve.

Figure 2K:
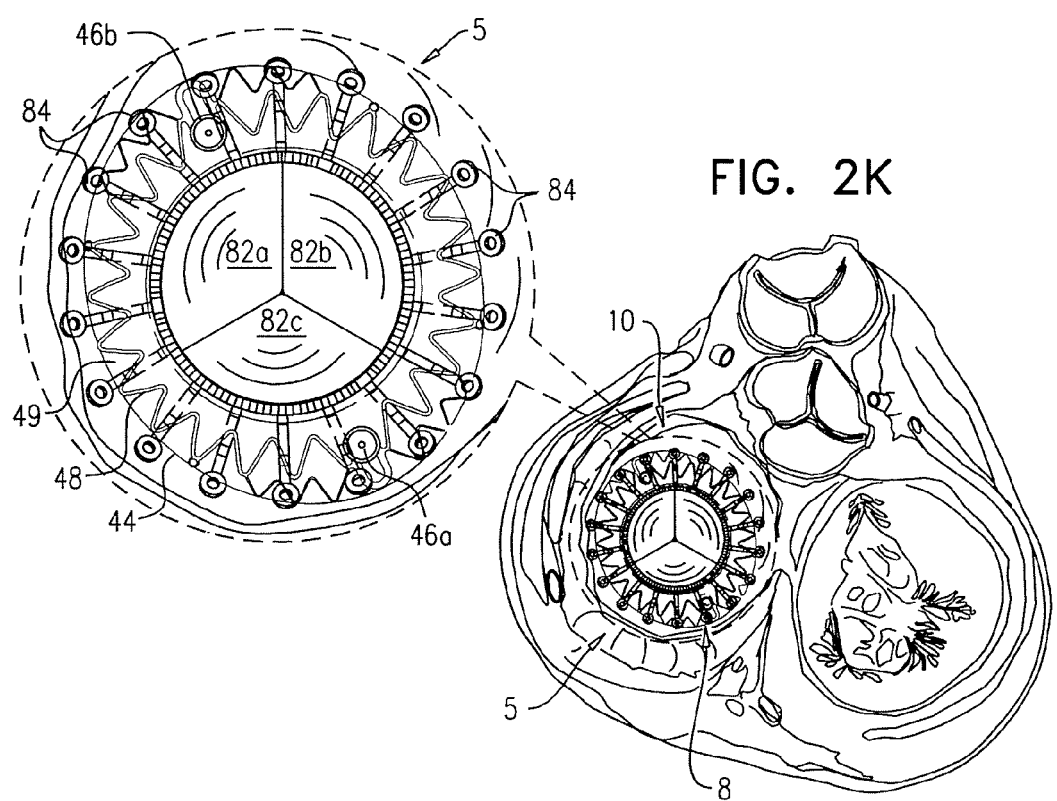

Reference is now made to FIG. 2K which shows a bird's-eye view of valve 80. Prosthetic valve 80 further comprises a plurality of valve leaflets 82, which may be artificial or tissue-based. The leaflets are typically coupled to an inner surface of the valve prosthesis. Leaflets 82 are coupled, e.g., sewn, to the frame and/or to the covering. For applications in which the prosthetic valve is configured to be implanted at the native mitral valve, the prosthetic valve typically comprises three leaflets 82a, 82b, and 82c, as shown in FIG. 2K.

Reference is now made to FIGS. 3A-C which are schematic illustrations of a system 120 comprising an invertible valve support 140, in accordance with some applications of the present invention. Invertible valve support 140 is identical to valve support 40 described herein, with the exception that the cylindrical element of valve support 140 is invertible, as is described hereinbelow. Additionally, the method of advancing toward and implanting valve support 140 at annulus 11 is identical to the methods of advancing toward and implanting valve support 40 at annulus 11, as described hereinabove.

Valve support 140 comprises an annular element 144 (that is identical to annular element 44 described hereinabove) and a cylindrical element 142. Cylindrical element 142 has a first end 150, a second end 152, and a cylindrical body 153 disposed between first and second ends 150 and 152. Cylindrical element 142 is attached to annular element 144 at first end 150 of cylindrical element 142.

During and following implantation of support 140 at annulus 11, as shown in FIG. 3A, cylindrical element 142 is disposed above annular element 144 in a manner in which second end 152 and cylindrical body 153 are disposed above annular element 144 and within atrium 4. One or more elongate guide members 146a and 146b are reversibly coupled to cylindrical element 142 in a vicinity of second end 152. Elongate guide members 146a and 146b facilitate (a) advancement of prosthetic valve 80 therealong and toward valve support 140, and (b) inversion of cylindrical element 142 toward ventricle 6 when at least a portion of valve 80 is deployed within ventricle 6 (as shown in FIG. 3B).

The configuration of valve support 140 as shown in FIG. 3A (i.e., the configuration in which cylindrical element 142 is disposed within atrium 4) eliminates the obstruction of native valve 5 and of leaflets 12 and 14 by any portion of valve support 140. In this manner, valve support 140 may be implanted at valve 5 while valve 5 resumes its native function and leaflets 12 and 14 resume their natural function (as shown by the phantom drawing of leaflets 12 and 14 in FIG. 3A which indicates their movement). This atrially-inverted configuration of valve support 140 reduces and even eliminates the amount of time the patient is under cardiopulmonary bypass. Only once prosthetic valve 80 is delivered and coupled to valve support 140 and cylindrical element 142 is thereby ventricularly-inverted, native leaflets 12 and 14 are pushed aside (FIG. 3B).

FIG. 3B shows the inversion of cylindrical element 142 by the partial positioning and deployment of prosthetic valve 80 within ventricle 6. Elongate guide members 146a and 146b are reversibly coupled to prosthetic valve 80 and extend within overtube 70. Following the full deployment of valve 80 and the coupling of valve 80 to valve support 140, elongate guide members 146a and 146b are decoupled from prosthetic valve 80 and from cylindrical element 142. For example, a cutting tool may be used to decouple elongate members 146a and 146b from the valve support 140. Alternatively, elongate members 146a and 146b may be looped through the cylindrical element 142, such that both ends of each elongate member 146a and 146b remain outside of the patient's body. The operating physician decouples elongate members 146a and 146b from valve support 140 by releasing one end of each of elongate members 146a and 146b and pulling on the other end, until elongate members 146a and 146b are drawn from valve support 140 and removed from within the body of the patient.

FIG. 3C shows prosthetic valve 80 coupled to valve support 140. Valve 80 is identical to the valve described hereinabove.

Figure 4A:
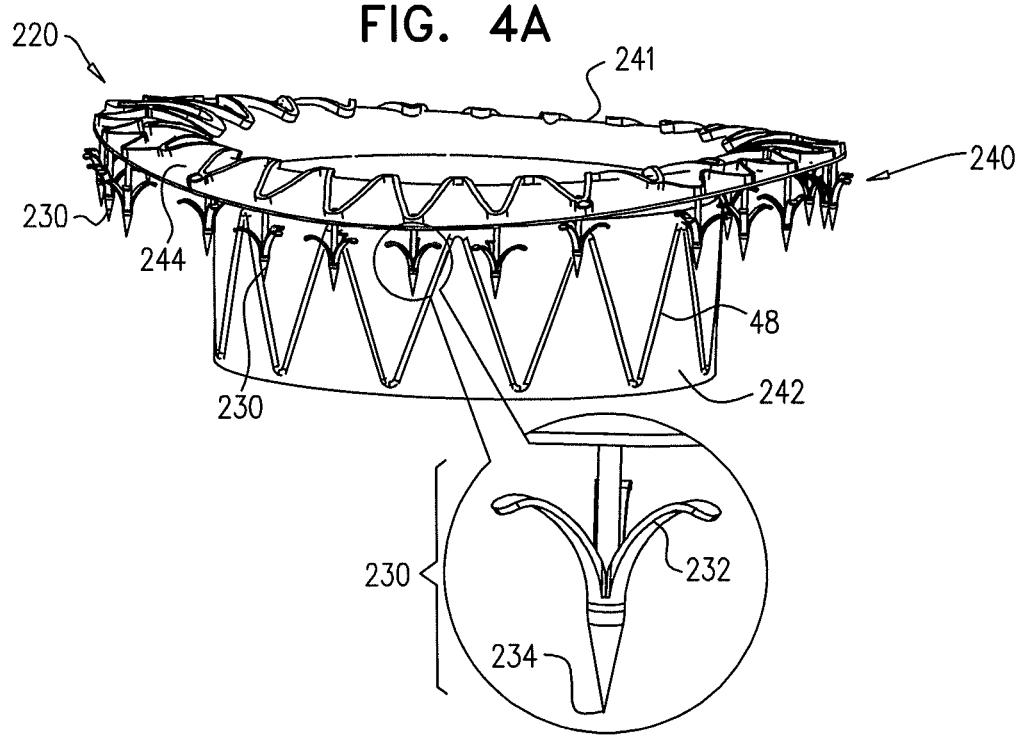
FIGS. 4A-B are schematic illustrations of a valve support coupled to a plurality of tissue anchors, in accordance with some applications of the present invention.
Figure 4B:
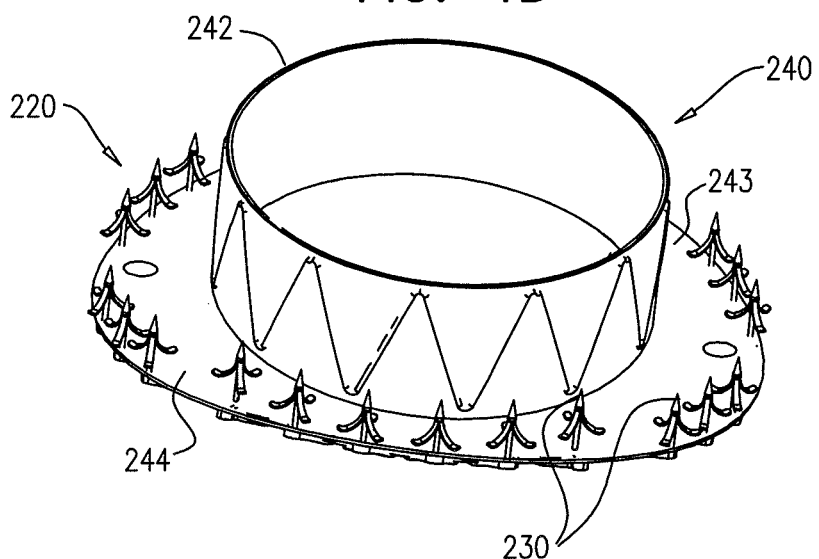

Reference is now made to FIGS. 4A-B which are schematic illustrations of a system 220 comprising a valve support 240 comprising an annular element 244 and a cylindrical element 242 and one or more (e.g., a plurality, as shown, of) tissue anchors 230, in accordance with some applications of the present invention. Annular element 244 has an upper surface 241 and a lower surface 243. Tissue anchors 230 are coupled to lower surface 234 of annular element. Tissue anchors 230 are shaped so as to define a pointed distal tip 234 and one or more (e.g., three, as shown) radially-expandable prongs 232. Prongs 232 comprise a flexible metal, e.g., nitinol or stainless steel, and have a tendency to expand radially. Anchors 230 facilitate coupling of valve support 240 to annulus 11 of native valve 5, such as the mitral valve or the tricuspid valve. Anchors 230 are typically distributed approximately evenly around lower surface 243 of annular element 244. For some applications, one or more anchors 230 are disposed at a location of annular element that is configured to be positioned adjacently to commissures 8 and 10 of valve 5.

Reference is now made to FIGS. 5A-D which are schematic illustrations of valve support 240 being implanted at valve 5 and the subsequent coupling of prosthetic valve 80 to valve support 240. Valve support 240 is advanced toward native valve 5 by pushing elements 52a and 52b, as described hereinabove with respect to valve support 40 with reference to FIGS. 2D-F. In response to the pushing force to valve support 240 by pushing elements 52a and 52b, anchors 230 are pushed into tissue of annulus 11 of valve 5. The pushing force by elements 52a and 52b is sufficient to implant each one of the plurality of anchors that are distributed around lower surface 243 of annular element 244.

Reference is made to FIG. 6, which is a schematic illustration of advancement of a guide member having a looped portion, toward commissures of a mitral valve, in accordance with some applications of the present invention. FIG. 6 shows only one guide member 21, looped through commissures 8 and 10 in a manner in which the guide member defines a looped portion 23 between commissures 8 and 10 (i.e., a portion of the guide member that is disposed in a ventricle 6 of heart 2), and first and second free ends which are disposed and accessible at a site outside the body of the patient, as described hereinabove with reference to FIGS. 1A-B.

FIG. 5A shows initial penetration of tissue of annulus 11 by pointed distal tip 234 of anchor 230. In FIG. 5B, the initial force of the tissue on prongs 232 pushes inwardly prongs 232. Finally, in FIG. 5C, prongs 232 expand within tissue of annulus 11 to assume a flower shape and a larger surface area to restrict proximal motion of anchor 230 and thereby anchor valve support 240 in tissue of annulus 11. As shown in FIGS. 5-C, the cylindrical element of valve support 240 pushes aside native leaflets 12 and 14 of valve 5.

In FIG. 5D, prosthetic valve 80 is coupled to valve support 240, in a manner as described hereinabove.

Reference is now made to FIGS. 1A-D, 2A-K, 3A-C, 4A-B and 5A-D. It is to be noted that valve supports 40 and 240 may be invertible as described hereinabove with respect to valve support 140 with reference to FIGS. 3A-C. It is to be further noted that valve supports 40 and 140 may be coupled to one or more, e.g., a plurality of tissue anchors 230, as described hereinabove with respect to valve support 140 with reference to FIGS. 4A-B and 5A-C. It is to be yet further noted that valve supports and prosthetic valves herein may be used to replace native mitral valves or native tricuspid valves.

Systems 20, 120, and 220 are advanced toward valve 5 in a transcatheter procedure, as shown. It is to be noted, however, that systems 20, 120, and 220 may be advanced using any suitable procedure, e.g., minimally-invasive or open-heart. It is to be further noted that systems 20, 120, and 220 may be used to replace them mitral valve, as shown, and the tricuspid valve (not shown), mutatis mutandis.

For some applications, techniques described herein are practiced in combination with techniques described in one or more of the references cited in the Background section of the present patent application.

Additionally, techniques described herein may be performed in combination with techniques described in one or more of the following patent application, all of which are incorporated herein by reference:

U.S. Provisional Patent Application 61/283,819 to Hacohen, entitled, "Foldable hinged prosthetic heart valve," filed on Dec. 8, 2009; and/or U.S. Provisional Patent Application 61/312,412 to Hacohen, entitled, "Prosthetic mitral valve with tissue anchors," filed on Mar. 10, 2010.

It will be appreciated by persons skilled in the art that the present invention is not limited to what has been particularly shown and described hereinabove. Rather, the scope of the present invention includes both combinations and subcombinations of the various features described hereinabove, as well as variations and modifications thereof that are not in the prior art, which would occur to persons skilled in the art upon reading the foregoing description.

The invention claimed is:

1. Apparatus, for use with a native atrioventricular valve of a patient, the native atrioventricular valve including leaflet tissue of at least two leaflets, the leaflets being connected to each other at one or more commissures, the apparatus comprising:

one or more sheaths, configured to be transluminally advanced to the native valve of the patient;

one or more valve support guide members, configured to be transluminally delivered via the one or more sheaths to the native atrioventricular valve;

one or more valve support anchors having at least two tissue-engaging surfaces, the valve support anchors being configured to be transluminally advanced, in a closed state thereof, to the native valve through at least one of the sheaths, to be opened to an open state thereof, at the native valve, by the tissue-engaging surfaces moving away from each other, and to subsequently be anchored to the leaflet tissue of the native valve;

a prosthetic valve support, disposable within one of the sheaths, and advanceable toward the native valve along the one or more valve support guide members, and configured to be placed at the native valve subsequently to the anchoring of the valve support anchors, and anchored to the leaflet tissue of the native valve by the valve support anchors; and a prosthetic valve configured to be advanced to the prosthetic valve support independently of the valve support guide members, and to be coupled to the valve support subsequently to the placing of the prosthetic valve support at the native valve.

2. The apparatus according to claim 1, wherein the valve support is collapsible for transcatheter delivery and expandable to contact the native atrioventricular valve.

3. The apparatus according to cairn 1, wherein the one or more valve support anchors are configured to be anchored to the leaflet tissue from ventricular surfaces thereof.

4. The apparatus according to claim 1, wherein the one or more valve support guide members comprises one valve support guide member that is looped through first and second commissures of the atrioventricular valve in a manner in which a looped portion of the valve support guide member is disposed in a ventricle of the patient and first and second free ends of the valve support guide member are accessible from a site outside a body of the patient.

5. The apparatus according to claim 1, wherein the one or more valve support anchors comprises first and second tissue anchors, the first and second tissue anchors being configured to be anchored to respective first and second commissures of the atrioventricular valve of the patient.

6. The apparatus according to claim 1, wherein:
the one or more valve support anchors each comprise one or more radially-expandable prongs, and
the one or more prongs are configured to be disposed within one of the sheaths in a compressed state prior to the anchoring, and exposed from within the sheath in order to expand and facilitate anchoring of the valve support anchor to the respective commissures.

7. The apparatus according to claim 1, wherein the prosthetic valve comprises two or more prosthetic leaflets.

8. The apparatus according to claim 1, wherein the native atrioventricular valve includes a mitral valve, and wherein the prosthetic valve comprises three prosthetic leaflets.

9. The apparatus according to claim 1, wherein the valve support guide members are removable from the patient following the anchoring of the prosthetic valve support at the atrioventricular valve.

10. The apparatus according to claim 1, wherein the valve support is shaped so as to define a distal portion which is configured to push aside, at least in part, native leaflets of the valve of the patient.

11. The apparatus according to claim 1, wherein the one or more valve support anchors are advanceable along the one or more valve support guide members.

12. The apparatus according to claim 1, wherein the valve support is shaped so as to define one or more holes, the one or more holes being configured to facilitate slidable passage therethrough of a respective one of the one or more valve support guide members.

13. The apparatus according to claim 1, wherein the prosthetic valve is shaped so as to define one or more snares configured to ensnare one or more of the native leaflets of the native valve of the patient.

14. The apparatus according to claim 1, wherein the one or more valve support anchors comprises one or more ventricular anchors, and wherein the apparatus further comprises one or more atrial anchors, each atrial anchor being configured to be advanced toward an atrial surface of the valve support and anchor in place the valve support in a vicinity of a respective one of the ventricular anchors.

15. The apparatus according to claim 1, further comprising one or more delivery tubes, slidable over a respective one of the valve support guide members, wherein:
each one of the one or more valve support anchors is removably coupled to a distal end of a respective one of the delivery tubes,
each delivery tube is configured to push the respective anchor through the at least one of the sheaths, and along the respective guide member, and
each delivery tube is decouplable from the respective anchor following the anchoring of the anchor to the leaflet tissue.

16. The apparatus according to claim 15, wherein the one or more valve support guide members are removable from the body of the patient following the pushing of the one or more anchors through the at least one of the sheaths.

17. The apparatus according to claim 15, wherein:
the valve support is shaped so as to define one or more holes,
the one or more holes are configured to facilitate slidable passage therethrough of a respective one of the one or more delivery tubes, and
the one or more delivery tubes are decoupleable from the respective valve support anchor following the anchoring of the valve support to the leaflet tissue.

18. The apparatus according to claim 17, wherein the one or more delivery tubes are removable from the body of the patient following the anchoring of the valve support to the leaflet tissue.

19. The apparatus according to claim 1, wherein the valve support comprises an annular element and a generally cylindrical element coupled to the annular element, the generally cylindrical element being configured to push aside the native leaflets of the native valve, and wherein the cylindrical element has first and second ends and a cylindrical body that is disposed between the first and second ends.

20. The apparatus according to claim 19, further comprising one or more annular element tissue anchors, wherein the annular element has an upper surface and a lower surface, and wherein the lower surface is coupled to the one or more annular element tissue anchors, the one or more annular element tissue anchors being configured to puncture tissue of a native annulus of the native valve of the patient.

21. The apparatus according to claim 20, wherein the one or more annular element tissue anchors comprises a plurality of annular element tissue anchors positioned around the lower surface of the annular element.

22. The apparatus according to claim 20, wherein the one or more annular element tissue anchors comprises a first commissural anchor configured to puncture tissue of the native valve at a first commissure thereof, and a second commissural anchor configured to puncture tissue of the native valve at a second commissure thereof.

23. The apparatus according to claim 20, wherein each anchor of the one or more annular element tissue anchors comprises a distal pointed tip and one or more radially-expandable prongs, the prongs being configured to expand and facilitate anchoring of the anchor and restrict proximal motion of the annular element tissue anchor.

24. The apparatus according to claim 19, further comprising one or more prosthetic valve guide members reversibly couplable to the cylindrical element in a vicinity of the second end of the cylindrical element, the prosthetic valve guide members being configured to facilitate advancement of the prosthetic valve therealong and toward the valve support.

25. The apparatus according to claim 24, wherein:
the first end of the cylindrical element is coupled to the annular element,
during a first period, the second end of the cylindrical element is disposed above the annular element in a manner in which the body of the cylindrical element is disposed above the annular element, and
the cylindrical element is invertible in a manner in which, during a second period, the second end of the cylindrical element is disposed below the annular element and the body of the cylindrical element is disposed below the annular element.

26. The apparatus according to claim 25, wherein:
the native valve has an annulus, and is disposed between an atrium of a heart of the patient, and a ventricle of the heart of the patient,
the valve support is configured such that, when the valve support is disposed at the native valve, during the first period, the second end of the cylindrical element is disposed in the atrium of the heart of the patient and the annular element is positioned along the annulus of the native valve,
the prosthetic valve is advanceable along the one or more prosthetic valve guide members into the ventricle of the heart of the patient, and
the apparatus is configured such that, in automatic response to the advancement of the prosthetic valve into the ventricle, the one or more prosthetic valve guide members are pulled into the ventricle and pull the second end and the body of the cylindrical element into the ventricle to invert the cylindrical element.

27. The apparatus according to claim 1, further including a guidewire, configured to be transluminally advanced to the native valve subsequently to the anchoring of the prosthetic valve support to the leaflet tissue, and configured to facilitate advancing of the prosthetic valve toward the prosthetic valve support.

28. The apparatus according to claim 1, wherein the valve support guide members are decouplable from the prosthetic valve support following the anchoring of the prosthetic valve support at the atrioventricular valve, and wherein the prosthetic valve is configured to be transluminally advanced to the native valve subsequently to decoupling of the valve support guide members from the prosthetic valve support.

29. The apparatus according to claim 1, wherein the one or more valve support anchors are generally blunt.

30. The apparatus according to claim 1, wherein the prosthetic valve is configured to be coupled to the prosthetic valve support by being expanded while a portion of the prosthetic valve is disposed within the prosthetic valve support, such that the prosthetic valve is held in place with respect to the prosthetic valve support responsively to radial forces acted upon the prosthetic valve support by the prosthetic valve.

* * * * *